(12) United States Patent
Ayer et al.

(10) Patent No.: US 10,590,480 B2
(45) Date of Patent: Mar. 17, 2020

(54) POLYMERASE VARIANTS

(71) Applicant: Roche Sequencing Solutions, Inc., Pleasanton, CA (US)

(72) Inventors: Aruna Ayer, Santa Clara, CA (US); Preethi Sarvabhowman, Santa Clara, CA (US); Dhruti Vasudev Dalal, Sunnyvale, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 259 days.

(21) Appl. No.: 15/443,964

(22) Filed: Feb. 27, 2017

(65) Prior Publication Data

US 2018/0245147 A1 Aug. 30, 2018

Related U.S. Application Data

(60) Provisional application No. 62/301,619, filed on Feb. 29, 2016.

(51) Int. Cl.
*C12Q 1/6869* (2018.01)
*C12N 9/12* (2006.01)

(52) U.S. Cl.
CPC ......... *C12Q 1/6869* (2013.01); *C12N 9/1252* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 9,266,109 | B2 | 2/2016 | Howell et al. |
| 2010/0035254 | A1 | 2/2010 | Williams |
| 2012/0071359 | A1 | 3/2012 | Sun |
| 2012/0322666 | A1 | 12/2012 | Pham et al. |
| 2013/0053544 | A1 | 2/2013 | Howarth |
| 2014/0113291 | A1 | 4/2014 | Bernick et al. |
| 2014/0134616 | A1 | 5/2014 | Davis et al. |
| 2015/0167072 | A1 | 6/2015 | Sun et al. |
| 2015/0368626 | A1 | 12/2015 | Vander Horn et al. |
| 2016/0222363 | A1 | 8/2016 | Ayer et al. |
| 2016/0267983 | A1 | 9/2016 | Bushnaq et al. |
| 2016/0333327 | A1 | 11/2016 | Ayer et al. |

FOREIGN PATENT DOCUMENTS

| | | |
|---|---|---|
| WO | 2006028508 A2 | 3/2006 |
| WO | 2011/097028 A1 | 8/2011 |
| WO | 2012083249 A2 | 6/2012 |
| WO | 2012129242 A2 | 9/2012 |
| WO | 2013188841 A1 | 12/2013 |
| WO | 2014074727 A1 | 5/2014 |
| WO | 2015/061511 A1 | 4/2015 |
| WO | 2015061510 A1 | 4/2015 |
| WO | 2016124543 A1 | 8/2016 |
| WO | 2016/183403 A2 | 11/2016 |
| WO | 2017148861 A1 | 9/2017 |
| WO | 2017148862 A1 | 9/2017 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
AFH27088, Pubmed, 2012, retrieved from the Internet at http://www.ebi.ac.uk/ena/data/view/AFH27088&display=text.
AFH27143, Pubmed, 2012, retrieved from the Internet: http://www.ebi.ac.uk/ena/data/view/AFH27143&display=text.
Altschul et al, Basic Local Alignment Search Tool, Journal of Molecular Biology, 1990, pp. 403-410, vol. 215.
Altschul, Stephen F. et al., Gapped BLAST and PSI-BLAST: a new generation of protein database search programs, Nucleic Acids Research, 1997, pp. 3389-3402, vol. 25, No. 17.
Gardner et al, 2012, "Rapid incorporation kinetics and improved fidelity of a novel class of 3'-OH unblocked reversible terminators", Nucleic Acids Research, 140(15):7404-7415.
Johnson, Kenneth A., 2010, "The kinetic and chemical mechanism of high-fidelity DNA polymerases", Biochimica et Biophysica Acta, 1804:1041-1048.
Kong et al, 1993, "Characterization of a DNA Polymerase form the Hyperthermophile Archaea Thermococcus litoralist", The Journal of Biological Chemistry, 268(3):1965-1975.
Kranaster et al, 2009, "Taking Fingerprints of DNA Polymerases: Multiplex Enzyme Profiling on DNA Arrays", Angewandte Chemie International Edition, 48(25):4625-4628.
Lawyer et al, Isolation, 1989, "Characterization, and Expression in *Escherichia coli* of the DNA Polymerase Gene from Thermus aquaticus", The Journal of Biological Chemistry, 264(11):6427-6437.
Li et al, 2014, "Structural Analysis and Optimization of the Covalent Association between SpyCatcher and a Peptide Tag", Journal of Molecular Biology, 426:309-317.
Volozhanstsev, et al., UniProt Submission 13PV37 9CAUD (Apr. 1, 2015) (Retrieved from the Internet Aug. 18, 2016.
Volozhantsev, et al. Molecular Characterization of Podoviral Bacteriophages Virulent for Clostridium perfringens and Their Comparison with Members of the Picovirinae. PloS One 2012, 7:e38283-e38283.
Written Opinion for PCT/EP2016/052068, dated Jan. 2, 2016.
Written Opinion for PCT/US2016/032258, dated Aug. 21, 2016.
Written Opinion for PCT/EP2017/054502, dated May 3, 2017.
Written Opinion for PCT/EP2017/054501, dated May 3, 2017.

(Continued)

*Primary Examiner* — Iqbal H Chowdhury
(74) *Attorney, Agent, or Firm* — Roche Sequencing Solutions, Inc.

(57) ABSTRACT

The present of disclosure provides variant Pol6 polymerase polypeptide, compositions comprising the Pol6 variant polypeptides, and methods for using the variant Pol6 polypeptides for determining the sequencing of nucleic acids, for example, by nanopore sequencing. The variant Pol6 polymerases possess decreased rates of dissociation of template from the polymerase-template complex, which result in increased processivity relative to the parental Pol6 polypeptides from which they are derived.

18 Claims, 3 Drawing Sheets

Specification includes a Sequence Listing.

(56) References Cited

OTHER PUBLICATIONS

Zakeri et al, 2010, "Spontaneous Intermolecular Amide Bond Formation between Side Chains for Irreversible Peptide Targeting", Journal of the American Chemical Society, 132:4526-4527.

Zakeri et al, 2012, "Peptide tag forming a rapid covalent bond to a protein, through engineering a bacterial adhesion", PNAS, 109(12):E690-E697 w/supporting figs (19 pp.).

Astier et al, Toward Single Molecule DNA Sequencing: Direct Identification of Ribonucleoside and Deoxyribonucleoside 5'-Monophosphates by Using an Engineered Protein Nanopore Equipped with a Molecular Adapter, Journal of the American Chemical Society, Dec. 30, 2005, Published online Dec. 30, 2005 at https://pdfs.semanticscholar.org/8d63/1eba6e52b49f99729640dcdced07ff263ebb.pdf, 10.1021/ja057123+.

Ausubel et al, Short Protocols in Molecular Biology, Current Protocols in Molecular Biology, 1992, Table of Contents, Second Edition, Greene Publishing Associates & John Wiley & Sons.

Ausubel, F.M. et al., Current Protocols in Molecular Biology, Wiley & Sons Inc., (1987-1994), vol. 1.

Dennler et al, Transglutaminase-Based Chemo-Enzymatic Conjugation Approach Yields Homogeneous Antibody-Drug Conjugates, Bioconjugate Chemistry, 2014, pp. 569-578, vol. 25.

Eid, J, et al., Real-Time DNA Sequencing from single Polymerase Molecules, Science, vol. 323, pp. 133-138 (2009).

Fiss, E.H. et al., DNA polymerases with improved reverse transcriptase activity, FASEB J, (2009), 482.4 / retrieved from the Internet: http://www.fasebj.org/doi/abs/10.1096/fasebj.23.1_supplement.482.4, vol. 23 No. 1 Suppl.

Fuller, C. et al, Real-time single-molecule electronic DNA sequencing by synthesis using polymer-tagged nucleotides on a nanopore array, PNAS, (2016), pp. 5233-5238, vol. 113, No. 19.

Hale et al, HarperCollins Dictionary of Biology, CarperCollins Dictionary of Biology, 1991, Cover, Synopsis from AbeBooks, (none).

Heck et al, Enzyme-catalyzed protein crosslinking, Appl Microbiol Biotechnol, 2013, pp. 461-475, vol. 97.

Horhota et al, Glycerol Nucleoside Triphosphates: Synthesis and Polymerase Substrate, Organic Letters, 2006, pp. 5345-5347, vol. 8, No. 23.

International Search Report and Written Opinion dated Jul. 7, 2017 in corresponding PCT/EP2017/054500 filed on Feb. 27, 2017, pp. 1-20.

Kranaster et al, One-step RNA pathogen detection with reverse transcriptase activity of a mutated thermostable Thermus aquaticus DNA polymerase, Biotechnology Journal, 2010, pp. 224-231, vol. 5, Issue 2.

Kumar et al, PEG-Labeled Nucleotides and Nanopore Detection for Single Molecule DNA Sequencing by Synthesis, Scientific Reports, 2012, pp. 1-8, vol. 2.

Ngo et al, Computational Complexity, Protein Structure Prediction, and the Levinthal Paradox, The Protein Folding Problem and Tertiary Structure Prediction, 1994, pp. 433, 492-495, unknown, Merz & Le Grand.

Rashidian, Mohammad et al., Enzymatic Labeling of Proteins: Techniques and Approaches, Bioconjugate Chemistry, 2013, pp. 1277-1294, vol. 24.

Saiki et al, Primer-Directed Enzymatic Amplification of DNA with a thermostable DNA polymerase, Science, Jan. 29, 2988, pp. 487-491, vol. 239, No. 4839.

Sambrook et al, Chapter 9: Preparation of Radiolabeled DNA and RNA Probes, Chapter 9: Molecular Cloning: A Laboratory Manual, 2001, Sections 9.63-9.75, vol. 2, Third Edition, Cold Spring Harbor Laboratory Press.

Sambrook et al, Molecular Cloning A Laboratory Manual, Molecular Cloning: A Laboratory Manual, 1989, Cover, Bibliography, Table of Contents, Third Edition, Cold Spring Harbor Laboratory Press.

Sambrook, J. et al, Molecular Cloning A Laboratory Manual, Molecular Cloning A Laboratory Manual, 1989, Bibliography pp. 1-2, Second Edition, Cold Spring Harbor Laboratory Press.

Sambrook, J. et al, Molecular Cloning A Laboratory Manual, Molecular Cloning A Laboratory Manual, 2001, 3rd edition, 1+2, Cold Spring Harbor Laboratory Press.

Singleton et al, Dictionary of Microbiology and Molecular Biology, Dictionary of Microbiology and Molecular Biology, 1994, cover, Second Edition, John Wiley and Sons, NY.

Singleton et al, Dictionary of Microbiology and Molecular Biology, Dictionary of Microbiology and Molecular Biology, Second Edition, 1987, Cover, Bibliography, Preface, Table of Contents, Note for the User, Second Edition, John Wiley and Sons.

Thapa et al, Native Chemical Ligation: A Boon to Peptide Chemistry, Molecules, 2014, pp. 14461-14483, vol. 19.

UniProt Submission 13PV37 9CAUD (Apr. 1, 2015) (Retrieved from the Internet Aug. 18, 2016).

Volozhantsev et al, AFH27113 Clostridium phage phiCPV4 DNA polymerase, Pubmed, May 28, 2012, (3 pages), (none).

Watson et al, Molecular Biology of the Gene, Molecular Biology of the Gene, 1987, Cover, Bibliography, Preface, Reviewers, Brief Contents, Detailed Contents, Fourth Edition, The Benjamin/Cummings Publishing Company, Inc., Menlo Park.

Wu et al, Sortase-Mediated Transpeptidation for Site-Specific Modification of Peptides, Glycopeptides, and Proteins, J Carbohyd Chem., 2012, pp. 48-66, vol. 31, No. 1.

\* cited by examiner

POLYMERASE VARIANTS

CROSS-REFERENCE

The present application claims the benefit of U.S. Provisional Patent Application Ser. No. 62/301,619, filed Feb. 29, 2016, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 23, 2017, is named 04338_532US1_SL.txt and is 52,850 bytes in size.

TECHNICAL FIELD

Modified DNA polymerases are provided. The DNA polymerases comprise mutations that enhance the processivity of the polymerases, in particular in methods for nanopore sequencing.

BACKGROUND

Nanopores have recently emerged as a label free platform for interrogating sequence and structure in nucleic acids. Data are typically reported as a time series of ionic current as DNA sequence is determined when an applied electric field is applied across a single pore controlled by a voltage-clamped amplifier. Hundreds to thousands of molecules can be examined at high bandwidth and spatial resolution.

A crucial obstacle to the success of nanopores as a reliable DNA analysis tool is the processivity, which affects average read length. This and other desirable properties can be enhanced by modifying polymerases to increase the amount of sequence information obtained from a sequencing reaction.

SUMMARY OF THE INVENTION

In one aspect, a variant Pol6 enzyme having polymerase activity is provided. The variant Pol6 enzyme comprises a polypeptide having an amino acid sequence at least 70% identical to full-length parent polypeptide of SEQ ID NO:2, and a modification at one or more positions selected corresponding to amino acids from V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577 T578, F579, T580, G581, S582, V583, T584, E585, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, C293, S294, I295, Y342, V436, S437, G438, Q439, E440, and E585. In some embodiments, the modification at one or more positions is a substitution to amino acid K, R, H, Y, F, W, and/or T. In some embodiments, the modification at one or more positions is selected from G438K, E565K, E585K, L731K, E585K-L731K, M738K, and E585K-M738K. In some embodiments, the modification produces a variant polypeptide having increased processivity relative to the parent polypeptide, in some embodiments, the increased processivity comprises a decrease in the rate of template dissociation that is at least two-fold less than that of the parental Pol6. In some embodiments, the processivity of the variant Pol6 comprises an increase in read length produced by the variant Pol6 that is greater than the read length produced by the unmodified parent Pol6. In some embodiments, the variant Pol6 further comprises amino acid substitutions D44A, S366A, T529M, and A547F. In some embodiments, the variant Pol6 is attached to a monomeric or an oligomeric nanopore.

In another aspect, a position comprising a variant Pol6 enzyme having polymerase activity is provided. In some embodiments, the composition comprises a variant Pol6 enzyme that comprises a polypeptide having an amino acid sequence at least 70% identical to full-length parent polypeptide of SEQ ID NO:2, and a modification at one or more positions selected corresponding to amino acids from V173, N175, N176, N177, I178, V179, Y180, S211, Y212, I214, Y338, T339, G340, G341. T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, E585, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585. In some embodiments, the modification at one or more positions is a substitution to amino acid K, R, H, Y, F, W, and/or T. In some embodiments, the modification at one or more positions is selected from G438K, E565K, E585K, L731K, E585K-L731K, M738K and E585K-M738K. In some embodiments, the modification produces variant polypeptide having increased processivity relative is the parent polypeptide. In some embodiments, the increased processivity comprises a decrease in the rate of template dissociation that is at least two-fold less than that of the parental Pol6. In some embodiments, the processivity of the variant Pol6 comprise increase in read length produced by the variant Pol6 that is greater than the read length produced by the unmodified parent Pol6. In some embodiments, the variant Pol6 further comprises amino acid substitutions D44A, S366A, T529M, and A547F. In some embodiments, the variant Pol6 is attached to a monomeric or an oligomeric nanopore.

In another aspect, a plurality of polynucleotides encoding a variant Pol6 enzyme is provided. In some embodiments, the plurality of polynucleotides encode a variant Pol6 enzyme that comprises a polypeptide having an amino acid sequence at least 70% identical to full-length parent polypeptide of SEQ ID NO:2, and a modification at one or more positions selected corresponding to amino acids from V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, E585, Y596, E587, G588, E590, F591, V667, L668, G669, Q670, L685, C687, C688, G689, L690, P691, S692, A694, L708, G709, Q717, R718, V721, I734, I737, I738, F739, D693, L731, F732, T733, T287, G288, M289, R290, T291, A292, S293, S294, I295, Y342, V436, S437, G438, Q439, E440, and E585. In some embodiments, the modification at one or more positions is a substitution to amino acid K, R, H, Y, F, W, and/or T. In some embodiments, the modification at one or more positions is selected from G438K, E565K, E585K, L731K, E585K-L731K, M738K, and E585K-M738K. In some embodiments, the modification produces a variant polypeptide having increased processivity relative to the parent polypeptide. In some embodiments, the increased processivity comprises a decrease in the rate of template dissociation that is at least two-fold less than that of the parental Pol6. In some embodiments, the processivity of the variant Pol6 comprises an increase in read length produced by the variant Pol6 that is greater than the read length produced by the unmodified parent Pol6. In some embodiments, the variant Pol6 further comprises amino acid substitutions D44A, S366A, T529M, and A547F.

In another aspect, provided is an expression vector comprising a polynucleotide encoding a variant Pol6 enzyme having polymerase activity. In some embodiments, the expression vector comprises any one of a plurality of polynucleotides that encode a variant Pol6 enzyme that comprises a polypeptide having an amino acid sequence at least 70% identical to full-length parent polypeptide of SEQ ID NO:2, and a modification at one or more positions selected corresponding to amino from V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, E585, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585. In some embodiments, the modification at one or more positions is a substitution to amino acid K, H, Y, F, W, and/or T. In some embodiments, the modification at one or more positions is selected from G438K, E565K, E585K, L731K, E585K-L731K, M738K, and E585K-M738I. In some embodiments, the modification produces a variant polypeptide having increased processivity relative to the parent polypeptide. In some embodiments, the increased processivity comprises a decrease in the rate of template dissociation that is at least two-fold less than that of the parental Pol6. In some embodiments, the processivity of the variant Pol6 comprises an increase in read length produced by the variant Pol6 that is greater than the read length produced by the unmodified parent Pol6. In some embodiments, the variant Pol6 further comprises amino add substitutions D44A, S366A, T529M, and A547F.

In another aspect, a plurality of host cells each transformed or transfected with an expression vector encoding a variant Pol6 enzyme having polymerase activity is provided. In some embodiments, variant Pol6 enzyme comprises a polypeptide having an amino acid sequence at least 70% identical to full-length parent polypeptide of SEQ ID NO:2, and a modification at one or more positions selected corresponding to amino acids from V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, E585, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585. In some embodiments, the modification at one or more positions is a substitution to amino acid K, H, Y, F, W, and/or T. In some embodiments, the modification at one or more positions is selected from G438K, E565K, E585K, L731K, E585K-L731K, M738K, and E585K-M738K. embodiments, the modification produces a variant polypeptide having increased processivity relative to the parent polypeptide. In some embodiments, the increased processivity comprises a decrease in the rate of template dissociation that is at least two-fold less than that of the parental Pol6. In some embodiments, the processivity of the variant Pol6 comprises an increase in read length produced by the variant Pol6 that is greater than the read length produced by the unmodified parent Pol6. In some embodiments, the variant Pol6 further comprises amino acid substitutions D44A, 5366A, T529M, and A547F.

In another aspect, a method is provided for preparing a variant Pol6 enzyme having polymerase activity. In some embodiments, the method comprises culturing host cells that transformed or transfected with an expression vector encoding any one of the variant Pol6 polymerases described herein. In some embodiments, the method provided is for preparing a variant Pol6 enzyme that comprises a polypeptide having an amino acid sequence at least 70% identical to full-length parent polypeptide of SEQ ID NO:2, and a modification at one or more positions selected corresponding to amino acids from V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, E585, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585. In some embodiments, the modification at one or more positions is a substitution to amino acid K, R, H, Y, F, W, and/or T. In some embodiments, the modification at one or more positions is selected from G438K, E565K, E585K, L731K, E585K-L731K, M738K, and E585K-M738K. In some embodiments, the modification produces a variant polypeptide laving increased processivity relative to the parent polypeptide. In some embodiments, the increased processivity comprises a decrease in the rate of template dissociation that is at least two fold less than that of the parental Pol6. In some embodiments, the processivity of the variant Pol6 comprises an increase in read length produced by the variant Pol6 that is greater than the read length produced by the unmodified parent Pol6. In some embodiments, the variant Pol6 further comprises amino acid substitutions D44A, S366A, T529M, and A547F. In some embodiments, the method further comprises isolating the variant Pol6 enzyme.

In another aspect, provided is a biochip for sequencing a nucleic acid sample. The biochip comprises a plurality of nanopore sequencing complexes which comprise a variant Pol6 polymerase as described elsewhere herein, wherein the variant polymerase is attached to nanopore formed in a membrane and disposed adjacent to an electrode. In some embodiments, the variant Pol6 enzyme that comprises a polypeptide having an amino acid sequence at least 70% identical to full-length parent polypeptide of SEQ ID NO:2, and a modification at one or more positions selected corresponding to amino acids from V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, E585, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585. In some embodiments, the modification at one or more positions is a substitution to amino acid K, R, H, Y, F, W, and/or T. In some embodiments, the modification at one or more positions is selected from G438K, E565K, E585K, L731K, E585K-L731K, M738K, and E585K-M738K. In some embodiments, the modification produces a variant polypeptide having increased processivity relative to the parent polypeptide. In some embodiments, the increased processivity comprises a decrease in the rate of template dissociation that is at least two-fold less than that of the parental Pol6. In some embodiments, the processivity of the variant Pol6 comprises an increase in read length produced by the variant Pol6 that is greater than the read length produced by the unmodified parent Pol6. In some embodiments, the variant Pol6 further comprises amino acid substitutions D44A, S366A, T529M, and A547F.

In another aspect, a method for nano ore sequencing a nucleic acid sample is provided. The method comprises (a) providing tagged nucleotides to a nanopore sequencing complex comprising a variant Pol6 as described elsewhere herein, wherein an individual Legged nucleotide of said tagged nucleotides contains a tag coupled to a nucleotide, which tag is detectable with the aid of the nanopore; (b) under a high concentration of salt, carrying out a polymerization reaction with the aid of the variant Pol6 enzyme of the nanopore sequencing complex, thereby incorporating an individual tagged nucleotide of the tagged nucleotides into a growing strand complementary to a single stranded nucleic acid molecule from the nucleic acid sample, and (c) detecting, with the aid of the nanopore, a tag associated with the individual tagged nucleotide during incorporation of the individual tagged nucleotide, wherein the tag is detected with the aid of the nanopore while the nucleotide is associated with the Pol6 polymerase: The variant Pol6 enzyme that comprises a polypeptide having an amino acid sequence at least 70% identical o full-length parent polypeptide of SEQ ID NO:2, and a modification at one or more positions selected corresponding to amino acids from V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, E585, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585. In some embodiments, the modification at one or more positions is a substitution to amino acid K, R, H, Y, F, W, and/or T. In some embodiments, the modification at one or more positions is selected from G438K, E565K, E585K, L731K, E585K-L731K, M738K, and E585K-M738K. In some embodiments, the modification produces a variant polypeptide having increased processivity relative to the parent polypeptide. In some embodiments, the increased processivity comprises a decrease in the rate of template dissociation that is at least two-fold less than that of the parental Pol6. In some embodiments, the processivity of the variant Pol6 comprises an increase in read length produced by the variant Pol6 that is greater than the read length produced by the unmodified parent Pol6. In some embodiments, the variant Pol6 further comprises amino acid substitutions D44A, S366A, T529M, and A547F. In some embodiments, the nucleic acid sample is double stranded DNA. In some embodiments, the nucleic acid sample is single stranded DNA. In some embodiments, the nucleic acid sample is reverse transcribed RNA. In some embodiments, the nanopore is a monomeric nanopore e.g. OmpG. In other embodiments, the nanopore is an oligomeric nanopore e.g. an alpha-hemolysin nanopore. In some embodiments the nanopore sequencing is performed at high concentration of salt that is at least 100 mM salt.

DETAILED DESCRIPTION

Figure 1:
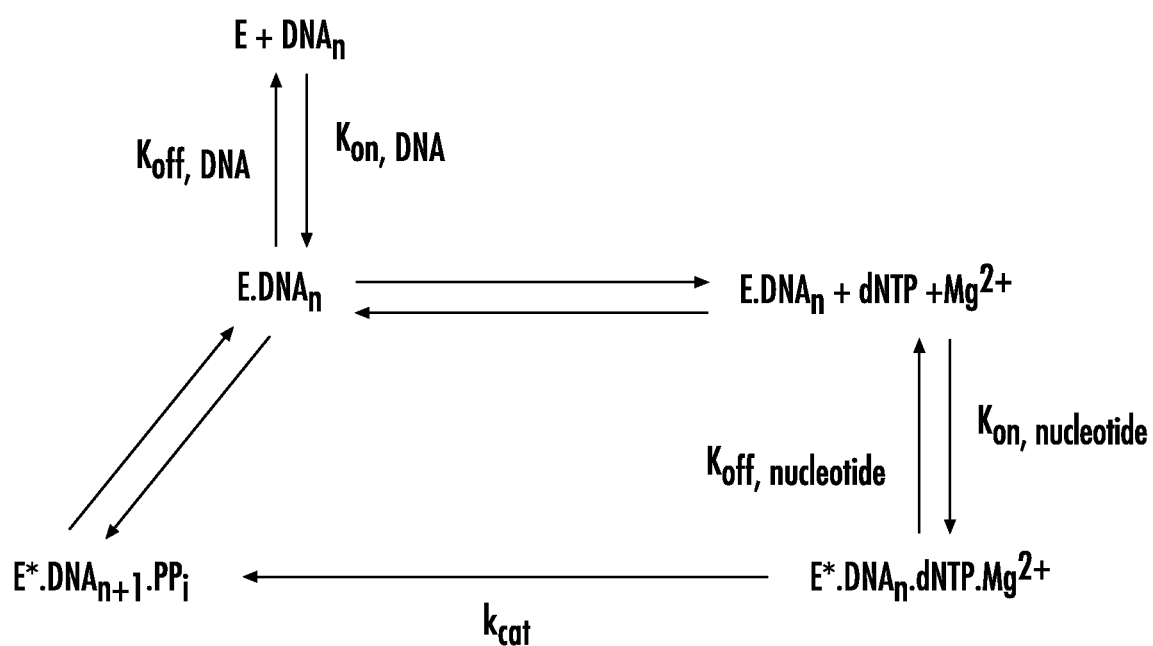
FIG. 1 illustrates the minimal catalytic steps required for single-nucleotide incorporation by DNA polymerase. The reaction begins with the binding of free DNA polymerase enzyme (E) to a duplex primer/template DNA complex ($DNA_n$) resulting in a binary enzyme-DNA complex (E•$DNA_n$). $k_{on,DNA}$ denotes the rate of association of the enzyme with the template; and $k_{off,DNA}$ denotes the rate of dissociation of the enzyme from the enzyme-DNA complex. The equilibrium determined by the $k_{on,DNA}$ and $k_{off}$.DNA rates defines the static processivity of the polymerase-template complex. Thus, the static processivity of the enzyme can be increased by an increase in the rate of association, $k_{on,DNA}$, and/or a decrease in the of dissociation, $K_{off,DNA}$. Addition of the correct nucleotide (dNTP) in the presence of divalent cations, such as $Mg^{2+}$, promotes the enzyme-DNA-dNTP ternary complex formation (E•$DNA_n$•dNTP•$Mg^{2+}$). The $k_{on, nucleotide}$ denotes the rate of nucleotide binding of the enzyme. The $k_{off, nucleotide}$ denotes the rate of nucleotide dissociation form the enzyme template complex. The equilibrium determined by the $k_{on, nucleotide}$ and $k_{off. nucleotide}$ defines the replicative processivity of the polymerase. Thus, the replicative processivity of the polymerase can be increased by an increase in the rate of nucleotide association, $k_{on, nucleotide}$, and/or a decrease in the rate of nucleotide dissociation, $k_{off, nucleotide}$. The binding of the dNTP induces the first conformational change of the enzyme in the ternary complex. A phosphodiester bond is formed between the a-phosphate of the incoming dNTP and the 3'-OH of the template/prime terminus to produce an added nucleotide base to the primer terminus (E*•$DNA_{n+1}$•$PP_i$). The reaction generates a pyrophosphate ($PR_i$) and a proton. A second conformational change allows for the release of the $PR_i$ to complete a cycle of nucleotide incorporation.

The invention w now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described Practitioners are particularly directed to Sambrook et al., 1989, and Ausubel FM et al., 1993, for definitions and terms of the art. It is to be understood that this invention is not limited to the particular methodology, protocols, and reagents described, as these may vary.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention, which can be had by reference to the specification as a whole. Accordingly, the terms defined immediately below are more fully defined by reference to the specification as a whole.

All patents and publications, including all sequences disclosed within such patents and publications, referred to herein are expressly incorporated by reference.

Definitions

The term "processivity" herein refers to the ability of a polymerase to remain attached to the template and perform multiple modification reactions. "Modification reactions" include but are not limited to polymerization, and exonucleolytic cleavage. In some embodiments, "processivity" refers to the ability of a DNA polymerase to perform a sequence of polymerization steps without intervening dissociation of the enzyme from the growing DNA chains. Typically, "processivity" of a DNA polymerase is measured by the number of nucleotides (for example 20 nts, 300 nts, 0.5-1 kb, or more) that are incorporated i.e., polymerized by a polymerase into a growing DNA strand prior to the dissociation of the DNA polymerase from the growing DNA strand. The processivity of DNA synthesis by a DNA polymerase is defined as the number of nucleotides that a polymerase can incorporate into DNA during a single template binding event, before dissociating from a DNA template. The overall efficiency of DNA synthesis increases when the processivity of a polymerase increases. "Processivity" can depend on the nature of the polymerase, the sequence of a DNA template, and reaction conditions, for example, salt concentration, temperature or the presence of specific proteins. As used herein, the term "high processivity" refers to a processivity higher than 20 nts (e.g. higher than 40 nts, 60 nts, 80 nts, 100 nts, 120 nts, 140 nts, 160 nts, 180 nts 200 nts, 220 nts, 240 nts, 260 nts, 280 nts, 300 nts, 320 nts, 340 nts, 360 nts, 380 nts, 400 nts, or higher) per association/dissociation with the template. The higher the processivity of a polymerase, that greater the number of nucleotides that can be incorporate prior to dissociation of the polymerase from the template, and therefore, the longer the sequence (read length) that can be obtained. Processivity can be measured according the methods defined herein and in WO 01/92501 A1 (MJ Bioworks, Inc., Improved Nucleic Acid Modifying Enzymes, published 6 Dec. 2001). Processivity encompasses static processivity and replicative processivity.

The term "static processivity" herein refers to the permanence of a polymerase-template complex in the absence of nucleotide incorporation i.e. in the absence of polynucleotide synthesis, as determined by the rate of association of polymerase with template, $k_{on,DNA}$, and the rate of dissociation of polymerase from the polymerase-template complex $k_{off-DNA}$. Static processivity is defined. In the absence of polynucleotide synthesis.

The term "replicative processivity" herein refers to the permanence of a polymerase-template complex in the during, nucleotide incorporation i.e. In the presence of polynucleotide synthesis, as determined by the rate of association of polymerase with template, $k_{on,nucleotide}$, and the rate of dissociation of polymerase from the polymerase-template complex $k_{off-nucleotide}$.

The term "association rate" when used in reference to a given polymerase herein refers to the rate at which a polymerase associates with a template. The association rate can be interpreted as a time constant for association ("$k_{on,DNA}$") of a polymerase with a nucleic acid template under a defined set of reaction conditions. Some exemplary assays for measuring the dissociation time constant of a polymerase are described further below. In some embodiments, the dissociation time constant can be measured in units of inverse time e.g., $sec^{-1}$ or $min^{-1}$.

The term "dissociation rate", when used in reference to a given polymerase, herein refers to the rate at which a polymerase dissociates from the template of the polymerase-template complex. The dissociation rate can be interpreted as a time constant for dissociation ("$k_{off,DNA}$") of a polymerase from a nucleic acid template under a defined set of reaction conditions. Some exemplary assays for measuring the dissociation time constant of a polymerase are described further below. In some embodiments, the dissociation time constant can be measured in units of inverse time, e.g., $sec^{-1}$ or $min^{-1}$.

The term "read length" herein refers to the number of nucleotides that a polymerase incorporates into a nucleic acid strand in a template-dependent manner prior to dissociation from the template.

The term "high concentration of salt" herein refers to a concentration of salt i.e. monovalent salt that is at least 100 mM and up to 1 M salt.

The terms "polynucleotide" and "nucleic acid" are herein used interchangeably to refer to a polymer molecule composed of nucleotide monomers covalently bonded in a chain Single stranded DNA (ss deoxyribonucleic acid, ssDNA), double stranded DNA (dsDNA) and RNA (ribonucleic acid) are examples of polynucleotides.

The term "amino acid" in its broadest sense, herein refers to any compound and/or substance that can be incorporated into a polypeptide chain. In some embodiments, an amino acid has the general structure $H_2N$—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid, "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

The term "nanopore sequencing complex" herein refers to a nanopore linked to an enzyme, e.g., a polymerase, which in turn is associated with a polymer, e.g., a polynucleotide or a protein. The nanopore sequencing complex is positioned in a membrane, e.g., a lipid bilayer, where it functions to identify polymer components, e.g., nucleotides or amino acids.

The term "enzyme-polymer complex" herein refers to an enzyme, polymerase that is associated/coupled with a polymer, e.g., polynucleotide or protein.

The term "enzyme-nanopore complex" herein refers to a nanopore that is associated/coupled with a sequencing enzyme e.g., a variant Pol6 polymerase. In some embodiments, the nanopore can be reversibly or irreversibly bound to the sequencing enzyme.

The terms "alpha-hemolysin," "α-hemolysin," "aHL," "a-HL" and "α-HL" are used interchangeably and herein refer to a protein that self-assembles into a heptameric water-filled transmembrane nanopore channel.

The term "OmpG" herein refers to an Outer Membrane Protein G monomeric nanopore.

The term "nucleotide" herein refers to a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pantose it is referred to as a nucleotide. A sequence of operatively linked nucleotides is typically referred to herein as a "base sequence" or "nucleotide sequence," and is represented herein by a formula whose left to right orientation is in the conventional direction of 5'-terminus to 3'-terminus.

The term "nucleotide analog" herein refers to analogs of nucleoside triphosphates, e.g., (S)-Glycerol nucleoside triphosphates (gNTPs) of the common nucleobases; adenine, cytosine, guanine, uracil, and thymidine (Horhota et al. Organic Letters, 8:5345-5347 [2006]).

The term "tag" herein refers to a detectable moiety that may be atoms or molecules, or a collection of atoms or molecules. A tag may provide an optical, electrochemical, magnetic, or electrostatic (e.g., inductive, capacitive) signature, which may be detected with the aid of a nanopore.

The term "tagged nucleotide" herein refers to a nucleotide having a tag attached at its terminal phosphate.

The term "sequencing enzyme" herein refers to the enzyme of a nanopore sequencing complex where it serves to identify polymer components, e.g., nucleotides or amino acids.

The term "polymerase" herein refers to an enzyme that catalyzes the polymerization of nucleotide (i.e., the polymerase activity). The term polymerase encompasses DNA polymerases, RNA polymerases, and reverse transcriptases. A "DNA polymerase" catalyzes the polymerization of deoxynucleotides. An "RNA polymerase" catalyzes the polymerization of ribonucleotides. A "reverse transcriptase" catalyzes the polymerization of deoxynucleotides that are complementary to an RNA template.

The terms "template DNA molecule" and "template strand" are used interchangeably herein to refer to a strand of a nucleic acid from which a complementary nucleic acid strand is synthesized by a DNA polymerase, for example, ire a primer extension reaction.

The term "sample polynucleotide" herein refers to a polynucleotide obtained from a sample, e.g., a biological sample.

The term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: Molecular Biology of the Gene, 4th Ed., W. A. Benjamin, Inc., Menlo Park, Calif. (1987)).

The term "nanopore" herein refers to a channel or passage formed or otherwise provided in a membrane. A membrane may be an organic membrane, such as a lipid bilayer, or a synthetic membrane, such as a membrane formed of a polymeric material. The nanopore may be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 Nm to about 1000 nm. Some nanopores are proteins, OmpG and alpha-hemolysin are examples of a protein nanopore.

The term "monomeric nanopore" herein refers to a nanopore protein that consists of a single subunit OmpG is an example of a monomeric nanopore.

The term "oligomeric nanopore" herein refers to nanopores that can be composed of multiple identical subunits, multiple distinct subunits, or a mixture of identical and distinct subunits. Nanopores with identical subunits are termed "homo-oligomeric nanopores". Nanopores containing two or more distinct polypeptide subunits are termed "hetero-oligomeric nanopores". Alpha-hemolysin is an example of an oligomeric nanopore.

The err "wild-type" herein refers to a gene or gene product (e.g., a protein) that has the characteristics of that gene or gene product when isolated from a naturally occurring source.

The term "parental" or "parent" herein refers to a protein, e.g., a nanopore or enzyme, to which modifications, e.g., substitution(s), insertion(s), deletion(s), and/or truncation(s) are made, to produce variants thereof. This term also refers to the polypeptide with which a variant is compared and aligned. The parent may be a naturally occurring (wild type) polypeptide, or it may be a variant thereof, prepared by any suitable means.

The term "mutation" herein refers to a change introduced into a parental sequence, including, but not limited to, substitutions, insertions, deletions (including truncations). The consequences of a mutation include, but are not limited to, creation of a new character, property, function, phenotype or trait not found in the parental sequence.

The term "variant" herein refers to a modified protein e.g., a variant Pol6 polymerase, which displays altered characteristics when compared to the parental protein, e.g., altered processivity.

The term "purified" herein refers to a polypeptide that is present in a sample at a concentration of at least 95% by weight, or at least 98% by weight of the sample in which it is contained.

Nomenclature

In the present description and claims, the conventional one-letter and three-letter codes for amino acid residues are used.

For ease of reference, polymerase variants of the application are described by use of the following nomenclature:

Original amino acid(s): position(s): substituted amino acid(s). According to this nomenclature, for instance the substitution of serine by an alanine in position 242 is shown as:

Glu585Lys or E585K

Multiple mutations are separated by plus signs, i.e.:

Glu585Lys+Leu731Lys or E585K+L731K representing mutations in positions 585 and 731 substituting glutamic acid and Leucine acid for Lysine end Leucine for Lysine, respectively.

When one or more alternative amino acid residues may be inserted in a given position it is indicated as: E585K/R or E585K or E585R.

Variant Pol6 Polymerase Polypeptides

In nanopore sequencing, high, salt concentrations boost the signal to noise ratio for ionic-current-based nanopore measurements. However, at high salt concentrations, the polymerase-DNA template complex becomes unstable, and leads to high polymerase turnover rates and diminished detection of sequential nucleotide additions i.e. length of sequence reads, during polymerization reactions.

The present disclosure provides variant Pol6 polymerase polypeptides, compositions comprising the Pol6 variant polypeptides, and methods for using the variant Pol6 polypeptides for determining the sequencing of nucleic adds, for example, by nanopore sequencing. The variant Pol6 polymerases possess decreased rates of dissociation of template from the polymerase-template complex, which result in increased processivity relative to the parental Pol6 polypeptides from which they are derived. The increased processivity is obtained at high salt concentrations, as described elsewhere herein.

The polymerase variants provided for herein can be used in the chip-based polynucleotide sequencing as described in WO2013/188841 (Genia Technologies, Inc., Chip Set-Up and High-Accuracy Nucleic Acid Sequencing, published 19 Dec. 2013).

Desired characteristics of a polymerase that finds use in sequencing DNA are:
a. Slow $k_{off\ nucleotide}$, and/or slow $k_{off,DNA}$
b. Fast $k_{on,nucleotide}$ and/or fast $k_{on,DNA}$
c. High fidelity
d. Low exonuclease activity
e. DNA strand displacement
f. $K_{chem}$
g. Increased stability
h. Increased processivity
i. Salt tolerance
j. Compatible with attachment to nanopore
k. Ability to incorporate a polyphosphates having 4, 5, 6, 7 or 8 phosphates, e.g., quadraphosphate, pentaphosphate, hexaphosphate, heptaphosphate or octophosphate nucleotide
l. Sequencing accuracy
m. Long read lengths, i.e., long continuous reads.

The Pol6 polymerase variants provided herein comprise modifications that are engineered to increase processivity, and which may be combined with additional modifications that impart or enhance one or more of the desired characteristics of a polymerase for sequencing polynucleotides e.g., DNA.

In one aspect, the disclosure provides variant Pol6 polymerase polypeptides that display increased processivity when compared to the parental polypeptides form which they are derived. The variant Pol6 polypeptides possess long, intrinsic, replicative porcessivity under native low salt conditions. As illustrated in FIG. 1, the processivity of a polymerase e.g. variant Pol6, is related to the static processivity and the replicative processivity. The static processivity is the ability of the polymerase-template complex to remain associated in the absence of polymerization of nucleotides, and is therefore dependent on the rates of association, $k_{on, DNA}$, and the rate of dissociation, $k_{off,\ DNA}$. Thus, static processivity can be, increased by an increase in $K_{on,\ DNA}$, and/or a decrease in $k_{off,\ DNA}$. In the presence of nucleotides and $Mg^{2+}$ the polymerase carries out sequential rounds of nucleotide incorporation until it dissociates from the polymerase-template complex, as determined by the polymerase's dissociation rate from the polymerase-template complex ($k_{off,\ DNA}$). The replicative processivity is the ability of the polymerase, when complexed with template, to incorporate nucleotides in a template-dependent manner. Thus, the overall processivity of the polymerase is dependent on tic and its replicative processivity. Thus, the, porcessivity of a polymerase can be increased by an increase in static processivity and/or replicative processivity.

In some embodiments, the parental polypeptide is a wild-type Pol6 polypeptide. The variant Pol6 polypeptides can be derived from a wild-type parental *Clostridium* phage phiCPV4 wild type sequence (SEQ ID NO:1) nucleic acid coding region plus a His-tag SEQ ID NO:1, protein coding region) and available elsewhere (National Center for Bioinformatics or GenBank Accession Numbers AFH27113). A wild-type parental Pol6 polymerase can be a homology of the parent Pol6 from *Clostridium* that can be used as a starting point for providing variant polymerases having increased processivity. It will be appreciated that other polymerases having a high degree of homology to the *Clostridium* phage sp. strain phiCPV4 may serve as a parental Pol6 without defeating the scope of the compositions and methods provided herein. Homologs of the parental Pol6 from *Clostridium* phage can share sequence identity with the Pol6 from *Clostridium* phage (SEQ ID NO:1) of at least 70%, at least 80%, at least 85%, at least 90%, at least 95%, at least 98%, or at least 99%. For example, a variant Pol6 can be derived from a homolog of the *Clostridium* phage that is at least 70% identical to the parental Pol6 from *Clostridium* phage.

In other embodiments, the variant Pol6 polypeptides can be derived from a variant parental Pol6. In some embodiments, the variant parental Pol6 polymerase is the Pol6 polymerase of SEQ ID NO: 2. In other embodiments, the variant parental Pol6 polymerase comprises modifications that remove/decrease the exonuclease activity of the polymerase (U.S. Provisional Application P529). In yet other embodiments, the polymerase can be mutated to reduce the rate at which the polymerase incorporates a nucleotide into a nucleic acid strand (e.g., a growing nucleic acid strand). In some cases, the rate at which a nucleotide is incorporated into a nucleic acid strand can be reduced by function lining the nucleotide and/or template strand to provide steric hindrance, such as, for example, through methylation of the template nucleic acid strand. In some instances, the rate is reduced by incorporating methylated nucleotides (P521). In other embodiments, the parental polypeptide is a Pol6 variant to which additional mutations have been introduced to improve the desired characteristics of a polymerase used in nanopore sequencing. The variant Pol6 can share sequence identity with the parental Pol6 of SEQ ID NO:2 of at least 70%, at least 80%, at least 85%, at least 90%, at least 95%, at least 98%, or at least 99%. The amino acid positions responsible for DNA interaction were predicted based on crystal structures of Phi29 bound to DNA template (Berman et al., EMBO J. 2007 Jul. 25; 26(14): 3494-3505).

In some embodiments, the modification of one or more amino acids at the DNA binding site can be one or more of a substitution, a deletion or an insertion, which modification(s) retain the polymerase activity of the variant polymerase, and decrease the of dissociation of polynucleotide from the Pol-DNA complex relative to that of the parent Pol6, The amino acid modification(s) can be made at one or more of amino acid residues corresponding to amino acid residues V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, E585, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585, of SEQ ID NO:2. In some embodiments, the variant Pol6 enzyme having polymerase activity, comprises an amino acid sequence at least 70% identical to that of the full-length parental Pol6 of SEQ ID NO:2, and has a modification at one or more of amino, acids corresponding to amino acid residues V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, E585, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585, of SEQ ID NO:2.

In some embodiments the mutation of one or more amino acids of the DNA binding site is a substitution to a positively charged amino acid. For example, any one or more of amino acids corresponding to amino acid residues V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585 of SEQ ID NO: 2 can be mutated to a K, R, or H. In some embodiments, the mutation of the one or more amino acids of the DNA binding site is a substitution to K. For example, the variant Pol6 polymerase can comprise amino one or both of amino add substitutions E585K, L731K, and M738K. In some embodiments the variant Pol6 polymerase comprises substitution E585K. In other embodiments, the Pol6 polymerase comprises substitutions E585K+L731K. In yet other embodiments, the Pol6 polymerase comprises substitutions E585K+M738K. In other embodiments, at least two, at least three, at least four, at least five, at least six amino acids or more of the DNA binding site are mutated. The resulting variant Pol6 enzymes retain polymerase activity, and display a decreased rate of dissociation of polynucleotide form the Pal-DNA complex relative to the rate of dissociation displayed in the parent polymerase that lacks the same mutations. In some embodiments, the modification of the parent Pol6 produces a variant Pol6 polymerase having a rate of dissociation from the template that is at least: 2-fold less that of the parent Pol6. Modifications of the parent Pol6 can produce variant Pol6 polymerases having a rate of dissociation from the template that is at least 3-fold less that of the parent Pol6, at least 4-fold less that of the parent Pol6, at least 5-fold less that of the parent Pol6, at least 6-fold less that of the parent Pol6, at least 7-fold less that of the parent Pol6, at least 8-fold less that of the patent Pol6, at least 9-fold less that of the parent Pol6, at least 10-fold less that of the parent Pol6.

The decreased rate of dissociation form template enables the production of longer reads. The average read length of the polymerized product produced by the variant Pol6 polymerases provided herein is greater than that produced by using the corresponding unmodified parental Pol6 polymerase. In some embodiments, the read length produced by the variant Pol6 polymerase is at least 100, at least 200, at least 300. at least 400, at least 500, or more nucleotides longer than the read obtained using the unmodified parent Pol6 polymerase.

In another aspect, the accuracy of the variant Pol6 polymerases provided herein can be measured in terms of zero-error reads obtained from the variant Pol6 polymerase reaction that are greater than 100, 200, 300, 400, 500, 750, 1000, 5000, 10000, 100000 nucleotides in length. The accuracy of the variant Pol6 polymerase, (including for example accuracy in a given sequencing reaction) can be measured in terms of the total number of "perfect" (i.e., zero-error) reads obtained from a polymerase reaction that are greater than 100, 200, 300, 400, 500, 750, 1000, 5000, 10000, 100000 nucleotides in length. The accuracy of the polymerase can be measured in terms of the longest perfect read (typically measured in terms of number of nucleotides included in the read) that is obtained from a polymerase reaction.

In some embodiments, a variant Pol6 polymerase can be assessed against a known or, reference polymerase under similar or identical conditions. In some embodiments, the conditions can include sequencing a nucleic acid molecule in the presence of high ionic strength solution. In some embodiments, the variant Pol6 polymerases provided herein catalyze DNA polymerization in solutions of high salt concentrations i.e. high salt solutions, at which they display the increased processivity relative to their parental Pol6. In some embodiments, the increased processivity is displayed at a high salt concentration that can be about 10, 20, 30, 40, 50, 60, 70, 80, 90, 108 150, 200, 250, 300, 350, 400, 450, 500, 550, 600, 650, 700, 750, 800 mM or grater. Typical salts include salts of metal elements. The high salt solutions can include one or more of a potassium salt, sodium salt, cesium salt, calcium salt, cobalt, nickel, aluminum, manganese, zinc, and lithium. Salts can also include the bicarbonate, sulfate, chloride, carbonate, nitrate, nitrite, bromide, citrate, acetate, cyanide, oxide or phosphate salt of a metal element known to those of skill in the art. In some embodiments, the salt is potassium glutamate (K-glu), potassium chloride (KCl), potassium sulfate ($K_2SO_4$), potassium nitrate ($KNO_3$), cesium chloride (CsCl), or cesium nitrate ($CsNO_3$). In some embodiments, the high salt solution includes K-Glu (potassium glutamate) or other monovalent salt. In addition, a mineral salt useful in the invention can include a mixture or blend of mineral salts. Blends of mineral salts that can be used in the invention include K-Glu and KCl, K-Glu and $K_2SO_4$, K-Glu and $KNO_3$, K-Glu and CsCl, K-Glu and $CsNO_3$, K-Glu and $KNO_3$, K-Glu and CsCl, K-Glu and $CsNO_3$, K-Glu and CsCl, K-Glu and $CsNO_3$, KCl and $K_2SO_4$, KCl and $KNO_3$, KCl and CsCl, KCl and $CsNO_3$, $K_2SO_4$, and $KNO_3$, $K_2SO_4$ and CsCl, $K_2SO_4$ and $CsNO_3$, $KNO_3$ and CsCl, $KNO_3$ and $CsNO_3$, and CsCl and $CsNO_3$. The foregoing salts may be used in the sequencing, polymerization reactions at a concentration in the range of 50 to 1M, in the range of 100 to 800 mM, in the range of 200 to 700 mM, in the range of 300 to 600 mM, in the range of 400 to 500 mM. In some embodiments, the high salt concentration can be of at least 150 mM and up to 500 mM. In other embodiments, the high concentration of salt can be greater than 500 mM.

The rate of polymerization of the variant Pol6 polymerases t high salt concentrations is at least 1 base/second, at least 5 bases/second, at least 10 bases/second, at least 20 bases/second, at least 30 base/second, at least 40 bases/second, at least 50 bases/second, or more. In some embodiments, the rate of polymerization of the variant Pol6 polymerase is at least 1 base/second at 100 mM salt, 1 base/second at 200 mM salt, at least 1 base/second at 300 mM salt, at least 1 base/second at 400 mM salt, at least 1 base/second at 500 mM salt, at least 1 base/second at 600 mM salt, at least 1 base/second at 700 mM salt, at least 1 base/second at 800 mM salt, at least 1 base/second at 800 mM salt, at least 1 base/second at 900 mM salt, at least 1 base/second at 1M salt. In some embodiments, the rate of polymerization of the variant Pol6 polymerase is between 1 and 10 bases/second at 100 mM salt, between 1 and 10 bases/second at 200 mM salt, between 1 and 10 bases/second at 300 mM salt, between 1 and 10 bases/second at 400 mM salt, between 1 and 10 bases/second at 500 mM salt, between 1 and 10 bases 600 mM salt, between 1 and 10 bases at 700 mM salt, between 1 and 10 bases/second at 800 mM salt, between 1 and 10 bases/second at 800 mM between 1 and 10 bases/second at 900 mM salt, or between 1 and 10 bases/second at 1M salt.

DNA Sequence Encoding Pol6 Variants

DNA sequences encoding a wild-type parent Pol6 may be isolated from any cell or microorganism producing the Pol6 in question, using various methods well known in the art.

Examples of DNA sequences that encode-wild-type *Clostridium* phage phiCPV4 i.e. wild-type Pol6, are provided herein as nucleotides 28-2220 of SEQ ID NO: 3, and as nucleotides 421 to 2610 of SEQ ID NO:5. In addition to the wild-type Pol6, SEQ ID NO: 3 comprises at its 5' end nucleotides that encode a histidine tag ($His_6$; HHHHHH; SEQ ID NO: 9), SEQ ID NO: 5 comprises at its 5' end nucleotides that encode histidine tag ($His_6$ (SEQ ID NO: 9)) and a SpyCatcher peptide SGDYDIPTTENLYFQGAM-VDTLSGLSSEQGQSGDMTIEEDSATHIKFSKRDEDG-KELAGATM ELRDSSGKTISTWISDGQVKDFYLYPG-KYTFVETAAPDGYEVATAITFTVNEQGQVTVNGKAT KGDAHI (SEQ ID NO: 10).

First, a genomic DNA and/or cDNA library can be constructed using chromosomal DNA or messenger RNA from the organism that produces the Pol6 to be studied. Then, if the amino acid sequence of the Pol6 is known, homologous, labeled oligonucleotide probes may be synthesized and used to identify Pol6-encoding clones from a genomic library prepared from the organism in question. Alternatively, a labeled oligonucleotide probe containing sequences homologous to a known Pol6 gene can be used as a probe to identify Pol6-encoding clones, using hybridization and washing conditions of lower stringency.

Alternatively, the DNA sequence encoding the Pol6 may be prepared synthetically by established standard methods, e.g. the phosphoroamidite method described by a S. L. Beaucage and M. H. Caruthers (1981) or the method described by Matthes et al, (1984). In the phosphoroamidite method, oligonucleotides are synthesized, e.g. in an automatic DNA synthesizer, purified, annealed, ligated and cloned in appropriate vectors.

Finally, the DNA, sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988), Site-Directed Mutagenesis Once a Pol6-encoding DNA sequence has been isolated or synthesized, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the Pol6-encoding sequence, or portion thereof, is created in a vector carrying the Pol6 gene Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al, (1954). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced. Other methods that effect site-directed mutagenesis include Kunkel's method, cassette mutagenesis, and PCR site-directed mutagenesis. Alternative methods for providing variants include gene shuffling, e.g., as described in WO 95122625 (from Affymax Technologies N.V.) or in WO 96/00343 (from Novo Nordisk A/S), or other corresponding techniques resulting in a hybrid enzyme comprising the mutation(s), e.g., substitution(s) and/or deletion(s), in question.

Expression of Pol6 Variants

A DNA sequence encoding an Pol6 variant can be used to express a Pol6, using an expression vector, which typically includes control sequences encoding a promoter, operator, ribosome binding site, translation initiation signal, and, optionally, a repressor gene or various activator genes. Examples of vectors that can be used for expressing variant Pol6 include the vectors of the pET expression system (Novagen).

A recombinant expression vector carrying DNA sequences may be any vector, which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

The procedures used to ligate the DNA construct encoding an Pol6 variant, and to insert it into suitable vectors containing the information necessary for replication, are well known to persons skilled in the art (cf., for instance, Sambrook et al., Molecular Cloning: A Laboratory Manual, Fourth Edition, Cold Spring Harbor, 2012).

A Pol6 variant can be produced in a cell that may be of a higher organism such as a mammal or an insect, but is preferably a microbial cell, e.g., a bacterial or a fungal (including yeast) cell. Examples of suitable bacteria are gram-negative bacteria such as *E. coli*, or gram-positive bacteria such as *Bacillus* sp., e.g. *Bacillus subtilis, Bacillus licheniformis, Bacillus lentus, Bacillus brevis, Geobacillus stearothermophilus, Bacillus alkalophilus, Bacillus amyloliquefaciens, Bacillus coagulans, Bacillus circulars, Bacillus lautus, Bacillus megaterium, Bacillus thuringiensis*, or *Streptomyces* sp., e.g. *Streptomyces lividans* or *Streptomyces murinus*. A yeast organism may be selected from a species of *Saccharomyces* or *Schizosaccharomyces*, e.g. *Saccharomyces cerevisiae*, or from a filamentous fungus *Aspergillus* sp., e.g. *Aspergillus oyzae* or *Aspergillus niger*. The host cell is typically bacterial and preferably *E. coli*.

In a further aspect, a method of producing Pol6 variant is provided, whirl method comprises cultivating a host cell as described above under conditions conducive to the production of the variant and recovering the variant from the cells and/or culture medium. The medium used to cultivate the cells may be any conventional medium suitable for growing the host cell in question and obtaining expression of the Pol6 variant. Suitable media are available from commercial suppliers or may be prepared according to published recipes (e.g., as described in catalogues of the American Type Culture Collection).

The Pol6 variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like. In some embodiments, purification of the variant Pol6 may be obtained by affinity chromatography of Pol6 polypeptides linked to an affinity tag. Several affinity or epitope tags that can be used in the purification of the Pol6 variants include hexahistidine tag (SEQ ID NO: 9), FLAG tag, Strep II tag, streptavidin-binding peptide (SBP) tag, calmodulin-binding peptide (CBP), glutathione S-transferase (GST), maltose-binding protein (MBP), S-tag, HA tag, and c-Myc tag. In some embodiments, a hexahistidine tag (SEQ ID NO: 9) is used in the purification of Pol6. The affinity tag can be covalently attached to the variant Pol6 polypeptide by a protein linker. Alternatively, the affinity tag can be encoded by the nucleic acid that comprises the sequence encoding the variant Pol6, and be expressed as a fusion protein. For example, in some embodiments, a $His_6$ tag (SEQ ID NO: 9) is expressed N-terminal to the variant Pol6 polypeptide (SEQ ID NO:2). In other embodiments, the $His_6$ tag (SEQ ID NO: 9) can be expressed adjacent to a linker e.g. SpyCatcher, and N-terminal to the Pol6 to provide a $His_6$-SpyCatcher-Pol6 polypeptide (SEQ ID NO:4). The SpyCatcher polypeptide can be covalently bound to a nanopore that comprises the SpyTag peptide AHIVMVDAYKPTK (SEQ ID NO:11).

Pol6 Nanopore Sequencing Complexes—Attachment of Pol6 to Nanopore

Nanopore sequencing with the aid of the variant Pol6 polymerases is accomplished by Pol6 nanopore sequencing complexes, which are formed by linking the variant Pol6 Polymerase to a nanopore. In some embodiments, a variant Pol6 polymerase is contacted with the sample DNA template to form the Pol6-DNA complex, which is subsequently linked to a nanopore to form the Pol6 nanopore sequencing complex. In other embodiments, the Pol6 polymerase is first attached to the nanopore and subsequently contacted with the sample DNA template to form the Pol6 nanopore sequencing complex. Methods for assembling nanopore sequencing complexes are described in U.S. Provisional Application No. 62/281,719 filed on Jan. 21, 2016.

Measurements of ionic current flow through a nanopore are made across a nanopore that have been reconstituted into a lipid membrane. In some instances, the nanopore is inserted in the membrane (e.g., by electroporation, by diffusion). The nanopore can be inserted by a stimulus signal such as electrical stimulus, pressure stimulus, liquid flow stimulus, gas bubble stimulus, sonication, sound, vibration, or any combination thereof. In some cases, the membrane is formed with aid of a bubble and the nanopore is inserted in the membrane with aid of an electrical stimulus. In other embodiments, the nanopore inserts itself into the membrane. Methods for assembling a lipid bilayer, forming a nanopore in a lipid bilayer, and sequencing, nucleic acid molecules can be found in PCT Patent Publication Nos. WO2011/097028 and WO2015/061510, which are incorporated herein by reference in their entirety.

The variant Pol6 alone or when complexed as a Pol6-DNA template complex can be attached to the nanopore prior to the nanopore being inserted into the lipid membrane or following the insertion of the nanopore into the lipid membrane.

The nanopores of the Pol6 nanopore sequencing complex include without limitation biological nanopores, solid state nanopores, and hybrid biological-solid state nanopores. Biological nanopores of the Pol6 nanopore sequencing complexes include OmpG from *E coli*, sp., *Salmonella* sp., *Shigella* sp., and *Pseudomonas* sp., and alpha hemolysin from *S. aureus* sp., MspA from *M. smegmatis* sp. The nanopores may be wild-type nanopores, variant nanopores, or modified variant nanopores.

Variant nanospores can be engineered to possess characteristics that are altered relative to those of the parental enzyme. See, for example, U.S. patent application Ser. No. 14/924,861 filed Oct. 28, 2015, entitled "alpha-Hemolysin Variants with Altered Characteristics" (which is incorporated by reference herein in its entirety). In some embodiments, the characteristics are altered relative to the wild-type enzyme. In some embodiments, the variant nanopore of the nanopore sequencing complex is engineered to reduce the ionic current noise of the parental nanopore from which it is derived. An example of a variant nanopore having an altered characteristic is the OmpG nanopore having one or more mutations at the constriction site (U.S. Provisional Patent Application No. 62/222,197, entitled "OmpG Variants", filed on Sep. 22, 2015, which is incorporated by reference herein in its entirety), which decrease the ionic noise level relative to that of the parent OmpG. The reduced ionic current noise provides for the use of these OmpG nanopore variants in single molecule sensing of polynucleotides and proteins. In other embodiments, the variant OmpG polypeptide can be further mutated to bind molecular adapters, which while resident in the pore slow the movement of analytes, nucleotide bases, through the pore and consequently improve the accuracy of the identification of the analyte (Aster et al.;, J Am Chem Soc 10.1021/ja057123+; published online on Dec. 30, 2005).

Modify variant nanopores are typically multimeric nanopores whose subunits have been engineered to affect intersubunit interaction (U.S. Provisional Patent Application Nos. 62/232,175 and 62/244,852, entitled "Alpha-Hemolysin Variants", filed on Sep. 24, 2015 and Oct. 22, 2015, respectively, which are incorporated by reference herein in their entirety). Altered subunit interactions can be exploited to specify the sequence and order with which monomers oligomerize to form the multimeric nanopore in a lipid bilayer. This technique provides control of the stoichiometry of the subunits that form the nanopore. An example of a multimeric nanopore whose subunits can be modified to determine the sequence of interaction of subunits during oligomerization is an aHL nanopore.

In some embodiments, a single Pol6, polymerase is attached to each nanopore. In other embodiments, two or more Pol6 polymerase are attached to a monomeric nanopore or to a subunit of an oligomeric nanopore.

Means of Attaching

The variant Pol6 alone or when complexed as a Pol6-DNA template complex can be attached to the nanopore in any suitable way. Attaching enzyme-polymer complexes to nanopores may be achieved using the SpyTag/SpyCatcher peptide system (Zakeri et al. PNAS109:E690-E697 [2012]) native chemical ligation (Thapa et al., Molecules 19:14461-14483 [2014]), sortase system (Wu and Guc, J Carbohydr Chem 31:48-66 [2012]; Heck et al., Appl Microbial Biotechnol 97:461-475 [2013]), transglutaminase systems (Dennler et al., Bioconjug Chem 25:569-578 [2014]), formylglycine linkage (Rashidian et al., Bioconjug Chem 24:1277-1294 [2013]), or other chemical ligation techniques known in the art.

In some instances, the variant Pol6 polymerase is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies, for example).

In some cases, zinc finger mutations are introduced into the nanopore molecule and then a molecule is used (e.g., a DNA intermediate molecule) to link the Pol6 polymerase to the zinc fin sites on the nanopore e.g. α-hemolysin.

Additionally, variant Pol6 alone or when complexed as a Pol6-DNA template complex enzyme-polymer complex, can be attached to a nanopore, e.g., aHL, OmpG, by means of a linker molecule that is attached to a nanopore at an attachment site. In some cases, the Pol6-DNA complex is attached to the nanopore with molecular staples. In some instances, molecular staples comprise three amino acid sequences (denoted linkers A, B and C). Linker A can extend from a nanopore monomer, Linker B can extend from the polymerase Won from the polymerase of the polymerase-DNA complex, and Linker C then can bind Linkers A and B (e.g., by wrapping around both Linkers A and B) and thus linking the variant polymerase Pol6 alone or as variant Pol6-DNA complex to the nanopore. Linker C can also be constructed to be part of Linker A or Linker B, thus reducing the number of linker molecules.

Other linkers that may find use in attaching the variant Pol6 polymerase to a nanopore are direct genetic linkage (e.g., $(GGGGS)_{1-3}$ amino acid linker (SEQ ID NO: 14)), transglutaminase mediated linking (e.g., RSKLG (SEQ ID NO: 15)), sortase mediated linking, and chemical linking through cysteine modifications. Specific linkers contemplated as useful herein are $(GGGGS)_{1-3}$ (SEQ ID NO: 14), K-tag (RSKLG (SEQ ID NO: 15)) on N-terminus, ΔTEV site (12-25), ΔTEV site+N-terminus of SpyCatcher (12-49).

An exemplary method for attaching a Pol6-DNA complex to a nanopore membrane involves attaching a linker molecule to a nanopore or mutating a nanopore to have an attachment site and then attaching a polymerase-polynucleotide complex to the attachment site or attachment linker. The polymerase-polynucleotide complex is attached to the attachment site or attachment linker after the nanopore is inserted in the membrane. In some cases, a polymerase-polynucleotide complex is attached to each of a plurality of nanopores that are inserted into a membrane and disposed over wells and/or electrodes of a biochip.

In some embodiments, the enzyme of the enzyme-polymer complex is expressed as a fusion protein that comprises a linker peptide. In some embodiments, a polymerase is the enzyme of the enzyme-polymer complex, and a polynucleotide is the polymer. The polymerase of the polymerase-polynucleotide complex is expressed as a fusion protein that comprises a SpyCatcher polypeptide, which can be covalently bound to a nanopore that comprises a SpyTag peptide (Zakeri et al. PNAS109:E690-E697 [2012]).

A variant Pol6-DNA complex may be attached to a nanopore using methods described, for example, in PCT/US2013/068967 (published as WO2014/074727; Genia Technologies, Inc.), PCT/US2005/009702 (published as WO2006/028508; President and Fellows of Harvard College), and PCT/US2011/065640 (published as WO2012/083249; Columbia University).

Biochips

Nanopores of the variant Pol6 nanopore sequencing complexes described herein may be inserted in a membrane, e.g., a lipid bilayer, and disposed adjacent or in proximity to a sensing electrode of a sensing circuit, such as an integrated circuit of a nanopore based sensor, e.g., a biochip. The nanopore may be inserted in a membrane and disposed of a well and/or sensing electrodes in the biochip. Multiple nanopore sensors may be provided as arrays. Biochips and methods for making biochips are described in PCT/US2014/061854 (published as WO2015/061511 Genia Technologies, Inc.), which is herein incorporated by reference in its entirety.

In one aspect, a biochip comprising a plurality of Pol6 nanopore sequencing complexes as described elsewhere herein, is provided. The biochip can comprise nanopores each having a variant Pol6 polymerase having increased processivity relative to the parental Pol6. The variant Pol6 comprises a modification at one or more amino acid residues corresponding to amino acid residues V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585 of the Pol6 of SEQ ID NO:2. In some embodiments, the modification is a substitution to amino acid K, R, and/or H. In some embodiments, the substitution is a substitution to K. In some embodiments, the variant Pol6 comprises the substitution E585K. In other embodiments, the variant Pol6 comprises the substitution of two amino acids E585K+L731K. In yet other embodiments, the variant Pol6 comprises the substitution of two amino acids E585K+L731K. The amino acid substitutions can be made in a parental Pol6 polymerase that comprises a His6 tag (SEQ ID NO. 9) and a SpyCatcher peptide as given the polymerase of SEQ ID NO:4.

The resulting variant Pol6 polymerases have increased processivity relative to their parental Pol6 polymerase. In some embodiments, the variant Pol6 polymerases have increased processivity at a high salt concentration. In some embodiments, the increased processivity is retained at a high salt concentration of 10, 20, 30, 40, 50, 60, 70, 80, 90, 100, 150, 200, 250, 300, 350, 400, 450, 500, 550. 600, 650, 700, 750, 800 mM or grater. In some embodiments, the increase in processivity is displayed at a high salt concentration of greater than 100 mM. The increase in processivity comprises a decrease in the rate of template dissociation that is at least 2-fold less that of the parent Pol6. Modifications of the parent Pol6 can produce variant Pol6 polymerases having a rate of dissociation from the template that is at least 3-fold less that of the parent Pol6, at least 4-fold less that of the parent Pol6, at least 5-fold less that of the parent Pol6, at least 6-fold less that of the parent Pol6, at least 7-fold less that of the parent Pol6, at least 8-fold less that of the parent Pol6, at least 9-fold less that of the parent Pol6, at least 10-fold less that of the parent Pol6.

For embodiments that, include an array of nanopores in a membrane, e.g., lipid bilayer, the density of sequencing nanopore complexes can be high. High density arrays are characterized as having a membrane surface that has a density of Pol6 nanopore sequencing complexes greater or equal to about to about 500 nanopore sequencing complexes per 1 mm². In some embodiments, the surface has a density of discrete nanopore sequencing complexes of about 100, about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 nanopore sequencing complexes per 1 mm². In some embodiments, the surface has a density of discrete nanopore sequencing complexes of at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 20000, at least about 40000, at least about 60000, at least about 80000, at least about 100000, or at least about 500000 nanopore sequencing complexes per 1 mm².

The methods of the invention involve the measuring of a current passing through the pore during interaction with the nucleotide. In some embodiments, sequencing a nucleic acid molecule can require applying a direct current (e.g., so that the direction at which the molecule moves through the nanopore is not reversed). However, operating a nanopore sensor for long periods of time using a direct current can change the composition of the electrode, unbalance the ion concentrations across the nanopore and have other undesirable effects. Applying an alternating current (AC) waveform can avoid these undesirable effects and have certain advantages as described below. The nucleic acid sequencing methods described herein that utilized tagged nucleotides are fully compatible with AC applied voltages and can therefore be used to achieve said advantages.

Suitable conditions for measuring ionic currents through transmembrane protein pores are known in the art and examples are provided herein in the Experimental section. The method is carried out with a voltage applied across the membrane and pore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 160 mV to 240 mV. It is possible to increase discrimination between different nucleotides by a pore of the invention by using an increased applied potential. Sequencing nucleic adds using AC waveforms and tagged nucleotides is described in US Patent Publication US2014/0134616 entitled "Nucleic Acid Sequencing Using Tags", filed on Nov. 6, 2013, which is herein incorporated by reference in its entirety. In addition to the tagged nucleotides described in US2014/0134616, sequencing can be performed using nucleotide analogs that lack a sugar or acyclic moiety e.g. (S)-Glycerol nucleoside triphosphates (gNTPs) of the four common nucleobases: adenine, cytosine, guanine, and thymidine (Horhota et al. Organic Letters, 8:5345-5347 [2006]).

Methods for Sequencing Polynucleotides

The molecules being characterized using the variant Pol6 polymerases of the Pol6 nanopore sequencing complexes described herein can be of various types, including charged or polar molecules such as charged or polar polymeric molecules. Specific examples include ribonucleic acid (RNA) and deoxyribonucleic acid (DNA) molecules. The DNA can be a single-strand DNA (ssDNA) or a double-strand DNA (dsDNA) molecule. Ribonucleic acid can be reversed transcribed then sequenced.

In one aspect, provided are methods for sequencing nucleic acids using the variant Pol6 polymerases described herein. In some embodiments, the methods comprise providing a variant Pol6 polymerase having a decreased rate of template dissociation, and attaching an isolated variant Pol6 polymerase-template complex to a nanopore inserted in a lipid membrane of a biochip to form a nanopore sequencing complex. In other embodiments, the sequencing methods comprise providing a variant Pol6 polymerase having a decreased rate of template dissociation, attaching the Pol6-template complex to a nanopore to provide a nanopore sequencing complex, and inserting the nanopore sequencing complex into a lipid membrane of a biochip.

The nanopore sequencing complexes comprising variant Pol6 polymerase can be used for determining the sequence of nucleic acids according to other nanopore sequencing platforms known in the art that utilize enzymes in the sequencing of polynucleotides. For example, nanopore sequencing complexes comprising the variant Pol6 polymerases described herein can be prepared according to the method described for sequencing nucleic acids according to the helicase and exonuclease-based methods of Oxford Nanopore (Oxford, UK), Illumina (San Diego, Calif.), and the nanopore sequencing-by-expansion of Stratos Genomics (Seattle, Wash.).

In some embodiments, sequencing of nucleic acids comprises preparing nanopore sequencing complexes comprising variant Pol6 polymerase enzyme described herein, and determining polynucleotide sequences using tagged nucleotides as is described in PCT/US2013/068967 (entitled "Nucleic Acid Sequencing Using Tags" filed on Nov. 7, 2013, which is herein incorporated by reference in its entirety). For example, a nanopore sequencing complex that is situated in a membrane (e.g., a lipid bilayer) adjacent, to or in sensing proximity to one or more sensing electrodes, can detect the incorporation of a tagged nucleotide by a polymerase as the nucleotide base is incorporated into a strand that is complementary to that of the polynucleotide associated with the polymerase, and the tag of the nucleotide is detected by the nanopore. The variant Pol6-DNA complex can be associated with the nanopore as provided herein.

Tags of the tagged nucleotides can include chemical groups or molecules that are capable of being detected by a nanopore. Examples of tags used, to provide tagged nucleotides are described at least at paragraphs [0414] to [0452] of PCT/US2013/068967. Nucleotides may be incorporated from a mixture of different nucleotides, e.g., a mixture of tagged dNTPs where N is adenosine (A), cytidine (C), thymidine (T), guanosine (G) or uracil (U). Alternatively, nucleotides can be incorporated from alternating solutions of individual tagged dNTPs, i.e., tagged dATP followed by tagged dCTP, followed by tagged dGTP, etc. Determination of a polynucleotide sequence can occur as the nanopore detects the tags as they flow through or are adjacent to the nanopore, as the tags reside in the nanopore and/or as the tags are presented to the nanopore. The tag of each tagged nucleotide can be coupled to the nucleotide base at any position including, but not limited to a phosphate (e.g., gamma phosphate), sugar or nitrogenous base moiety of the nucleotide. In some cases, tags are detected while tags are associated with a polymerase during the incorporation of nucleotide tags. The tag may continue to be detected until the tag translocates through the nanopore after nucleotide incorporation and subsequent cleavage and/or release of the tag. In some cases, nucleotide incorporation events release tags from the tagged nucleotides, and the tags pass through a nanopore and are detected. The tag can be released by the polymerase, or cleaved/released in any suitable manner including without limitation cleavage by an enzyme located near the polymerase. In this way, the incorporated base may be identified (i.e., A, C, G, T or U) because a unique tag is released from each type of nucleotide (i.e., adenine, cytosine, guanine, thymine or uracil). In some situations, nucleotide incorporation events do not release tags. In such a case, a tag coupled to an incorporated nucleotide is detected with the aid of a nanopore. In some examples, the tag can move through or in proximity to the nanopore and be detected with the aid of the nanopore.

In some cases, tagged nucleotides that are not incorporated pass through the nanopore. The method can distinguish between tags associated with un-incorporated nucleotides and tags associated with incorporated nucleotides based on the length of time the tagged nucleotide is detected by the nanopore. In one embodiment, an un-incorporated, nucleotide is detected by the nanopore for less than about 1 millisecond and an incorporated nucleotide is detected by the nanopore for a: least about 1 millisecond.

Thus, in one aspect, the disclosure provides for a method for sequencing a polynucleotide from a sample, e.g. a biological sample, with the aid of a variant Pol6 polymerase nanopore sequencing complex. The sample polynucleotide is combined with the variant Pol6 polymerase, to provide the variant Pol6 enzyme-polymer complex portion of the nanopore sequencing complex. In one embodiment, the sample polynucleotide is a sample ssDNA strand, which is combined with a DNA polymerase to provide a DNA polymerase-DNA complex. The variant Pol6 DNA polymerase-sample ssDNA strand is subsequently attached to a nanopore that has been inserted into a membrane e.g. a lipid bilayer, to provide the nanopore sequencing complex. The nanopore Portion of the sequencing complex is positioned in the membrane adjacent to or in proximity of a sensing electrode, as described elsewhere herein. The resulting nanopore sequencing complex is capable of determining the sequence of nucleotide bases of the sample DNA as described elsewhere herein. In other embodiments, the nanopore sequencing complex determines the sequence of double stranded DNA. In other embodiments, the nanopore sequencing complex determines the sequence of single stranded DNA. In yet other embodiments, nanopore sequencing complex determines the sequence of RNA by sequencing the reverse transcribed product. In one embodiment, the method provides for sequencing a nucleic acid sample with the aid of a biochip comprising a plurality of Pol6 nanopore sequencing complexes.

In some embodiments, a method for nanopore sequencing nucleic acid sample is provided. The method comprises using nanopore sequencing complexes comprising the variant Pol6 polymerases provided herein. In one embodiment, the method comprises providing tagged nucleotides to a Pol6 nanopore sequencing complex, and under high salt conditions, carrying out a polymerization reaction to incorporate the nucleotides in a template-dependent manner, and detecting the tag of each of the incorporated nucleotides to determine the sequence of the template DNA.

In one embodiment, tagged nucleotides are provided to a Pol6 nanopore sequencing complex comprising a variant Pol6 polymerase provided herein, and under conditions of high salt, carrying out a polymerization reaction with the aid of the variant Pol6 enzyme of said nanopore sequencing complex, to incorporate tagged nucleotides into a growing strand complementary to a single stranded nucleic acid molecule from the nucleic acid sample, and detecting, with the aid of nanopore, a tag associated with said individual tagged nucleotide during incorporation of the individual tagged nucleotide, wherein the tag is detected with the aid of said nanopore while the nucleotide is associated with the variant Pol6 polymerase.

Other embodiments of the sequencing method that comprise the use of tagged nucleotides with the present nanopore sequencing complexes for sequencing polynucleotides are provided in WO2014/074727, which is incorporated herein by reference in its entirety.

Sequencing nucleic acids using AC waveforms and tagged nucleotides is described in US Patent Publication US2014/0134616 entitled "Nucleic Acid Sequencing Using Tags", filed on Nov. 6, 2013, which is herein incorporated by reference in its entirety. In addition to the tagged nucleotides described in US2014/0134616, sequencing can be performed using nucleotide analogs that lack a sugar or acyclic moiety, e.g., (S) Glycerol nucleoside triphosphates (gNTPs)

of the five common nucleobases: adenine, cytosine, guanine, uracil, and thymidine (Horhota et al. Organic Letters, 8:5345-5347 [2006]).

Reagents and Kits

Sequencing reagents for DNA sequencing or amplification e.g. nanopore sequencing are also provided, the reagent(s) comprising a variant Pol6 polymerase having at least 70% identity to full-length parent polypeptide of SEQ ID NO:2 that comprises one or more amino acid substitutions of amino acid residues corresponding to amino acids V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585 of SEQ ID NO: 2. In some embodiments, the amino acids substitution(s) is to K, R, and/or H. In some embodiments, the sequencing reagent comprises the variant Pol6 polymerase of SEQ ID NO:6, SEQ ID NO:7 or SEQ ID NO:8, In some embodiments, the sequencing reagent comprises a polynucleotide encoding any one of the variant salt tolerant Pol6 polymerases provided herein.

In another aspect, provided is a kit comprising a sequencing reagent for DNA sequencing provided herein. In some embodiments, the kit further comprises a buffer and/or nucleotides.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds).

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes, Example 1

Directed Mutagenesis

Site directed mutagenesis was performed to mutate one or more amino acids of the putative DNA binding site of parental variant Pol6-44-X1 polymerase (SEQ ID NO:4), Pol6-44-X1 was derived from wild-type Pol6 to comprise the following substitutions: (Pol6-S366A T529M A547F D44A).

DNA of SEQ ID NO:4 encoding the variant polymerase pol6-44-X1 (SEQ ID NO:5) was purchased from a commercial source (DNA 2.0, Menlo Park, Calif.). The sequence was verified by sequencing.

The Pol6-44-X1 was expressed as a fusion protein having an N-terminal His-tag (underlined sequence in SEQ ID NO:4) and SpyCatcher domain (bolded italic sequence in SEQ ID NO:4).

The Pol6-44-X1 polymerase variant (SEQ ID NO:4) was derived from wild-type pol6 (SEQ ID NO:2), and the numbering of the amino acid mutations described for Pol6 D44A-X1 refer to the amino acid positions of SEQ ID NO:2. Rational positions to impact Pol6 processivity were identified based on analysis of Phi 29 crystal structure in its apo form, DNA bound form and DNA-nucleotide form (Berman et al. 2007).

For the primary screen, each of the rational positions were mutated to Lys (K) using the New England Biolabs Q5 mutagenesis protocol (Ipswich, Mass.). The following amino acids were mutated to Lys: V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, Y596, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585.

Combinations of substitutions to Lys (K) at two or more of amino acids V173, N175, N176, N177, I178, V179, Y180, S211, Y212, I214, Y338, T339, G340, G341, T343, H344, A345, D417, I418, F419, K420, I421, G422, G434, A436, Y441, G559, T560, Q662, N563, E566, E565, D568, L569, I570, M571, D572, N574, G575, L576, L577, T578, F579, T580, G581, S582, V583, T584, Y596, E587, G588, E590, F591, V667, L668, G669, Q670, L685, C687, C688, G689, L690, P691, S692, A694, L708, G709, Q717, R718, V721, I734, I737, M738, F739, D693, L731, F732, T733, T287, G288, M289, R290, T291, A292, S293, S294, I295, Y342, V436, S437, G438, Q439, E440, and E585,were also generated.

The primers for each mutagenesis reaction was designed using the NEB base changer protocol and ordered in 96-well plate format from IDT.

The forward and reverse primers were 5' phosphorylated in high throughput (HTP) format using the T4 polynucleotide kinase (PNK) purchased from NEB. A typical 25-μl reaction contained 15 μl of primer at 10 μM, 5 μl of 5× reaction buffer (from NEB), 1.25 μl PNK enzyme, 3.75 μl water. The reaction was performed at 37° C. for 30 min and the enzyme heat inactivated at 65° C. for 20 min.

PCR mutagenesis eras performed using Q5 DNA polymerase from NEB. A typical 25 μl reaction contained 5 μl of Q5 buffer, 5 μl of GC enhancer, 0.5 μl of 10 mM dNTPs, 1.25 μl of 18 μM phosphorylated mutagenesis primers forward and reverse, 0.26 μl Q5 polymerase and 1 μl of 5 ng/ml wild type Pol6 template, i.e., His-Pol6, and 10.75 μl H₂O.

Once PCR was completed, 0.5 μl of Dpn1 was added to 25 μl PCR mix and incubated at 37° C. for 1 hr.

2.5 μl of Blunt/TA ligase master mix were added to 2.5 μl of Dpn1 treated PCR product, and the reaction mixture was incubated at room temperature for 1 hr.

1 µl of ligation mix was added to 20 ul of 96-well BL21DE3 cells (EMD Millipore) and incubated on ice for 5 min.

The cells were heat shocked at 42° C. exactly 30 sec using the PCR thermocycler and placed on ice for 2 min.

80 µl of SOC were added to the cells, which were then incubated at 37° C. for 1 hr without shaking.

100 µl of SOC or ultra pure water were added to the cells, which were then plated on 48-well LB-agar plates comprising 50-100 µg/ml kanamycin. Cells were grown overnight at 37° C.

Example 2

Expression and Purification

Variants of the parental polymerase Pol6-44-X1 (SEQ ID NO:4) were expressed and purified using a high throughput method as follows.

DNA encoding variants in expression plasmid pD441 vector was transformed into competent *E. coli*, and glycerol stocks of the transformed cells were made. Starting from a tiny pick of the glycerol stock, grow 1 ml starter culture in LB with 0.2% Glucose and 100 µg/ml Kanamycin for approximately 8 hrs. Transfer 25 µl of log phase starter culture into 1 ml of expression media (Terrific Broth (TB) autoinduction media supplemented with 0.2% glucose, 50 mM Potassium Phosphate, 5 mM MgCl2 and 100 µg/ml Kanamycin) in 96-deep well plates. The plates were incubated with shaking at 250-300 rpm for 36-40 hrs at 28° C.

Cells were then harvested via centrifugation at 3200×g for 30 minutes at 4° C. The media was decanted off and the call pellet resuspended in 200 µl pre-chilled lysis buffer (20 mM Potassium Phosphate pH 7.5, 100 mM NaCl, 0.5% Tween20, 5mM TCEP, 10 mM Imidazole, 1 mM PMSF, 1× Bug Buster, 100 µg/ml Lysozyme and protease inhibitors) and incubate at room temperature for 20 min with mild agitation. Then add 20 µl from a 10× stock to a final concentration of 100 µg/ml DNase, 5 mM MgCl2, 100 µg/ml RNase I and incubate in on ice for 5-10 min to produce a lysate. Supplement the lysate with 200 µl of 1M Potassium Phosphate, pH 7.5 (Final concentration will be about 0.5M Potassium phosphate in 400 µl lysate) and filter through Pall filter plates (Part #5053, 3 micron filters) via centrifugation at approximately 1500 rpm at 4 C for 10 minutes. The clarified lysates were then applied to equilibrated 98-well His-Pur Cobalt plates (Pierce Part #90095) and bind for 15-30 min.

The flow through (FT) was collected by centrifugation at 500×G for 3 min. The FT was then washed 3 times with 400 ul of wash buffer 1 (0.5 M Potassium Phosphate pH 7.5, 1 M NaCl 5 mM TCEP, 20 mM Imidazole+0.5% Tween20). The FT was then washed twice in 400 µl wash buffer 2 (50 mM Tris pH 7.4, 200 mM KCl, 5 mM TCEP, 0.5% Tween20, 20 mM Imidazole).

The Pol6 was eluted using 200 µl elution buffer (50 mM Tris pH 7.4, 200 mM KCl, 5 mM TCEP, 0.5% Tween20, 300 mM Imidazole, 25% Glycerol) and collected after 1-2 min incubation. Reapply eluate to the same His-Pur plate 2-3 times to get concentrated Pol6 in elute. The purified polymerase is >95% pure as evaluated by SDS-PAGE. The protein concentration is ~3 uM (0.35 mg/ml) with a 260/280 ratio of 0.6 as evaluated by Nanodrop.

Polymerase processivity was verified by fluorescence displacement assay (see Example 3 as a function of the rate of dissociation from the polynucleotide template.

Example 3

Static Processivity Assay

The effect of mutations of amino acids of the DNA-binding site of variant polymerase Pol6-44-X1 i.e. Pol6-44-D44A, on the processivity of the variant polymerase was analyzed using a static processivity assay whereby the dissociation of DNA template from the variant polymerases was determined in the absence of polynucleotide synthesis.

Figure 2:
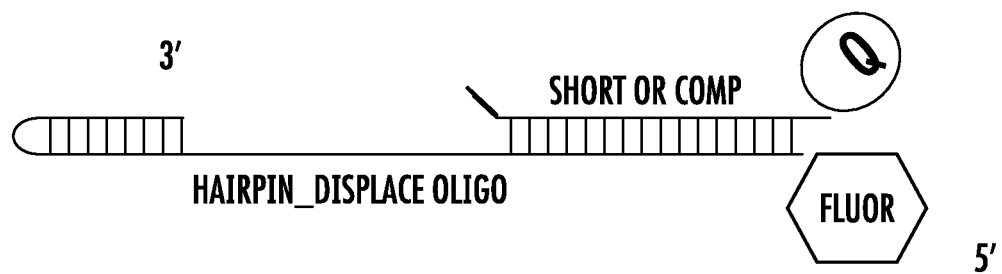
FIG. 2 illustrates an exemplary template used in the displacement assay. Reference is made to Example 3.
Figure 3A:
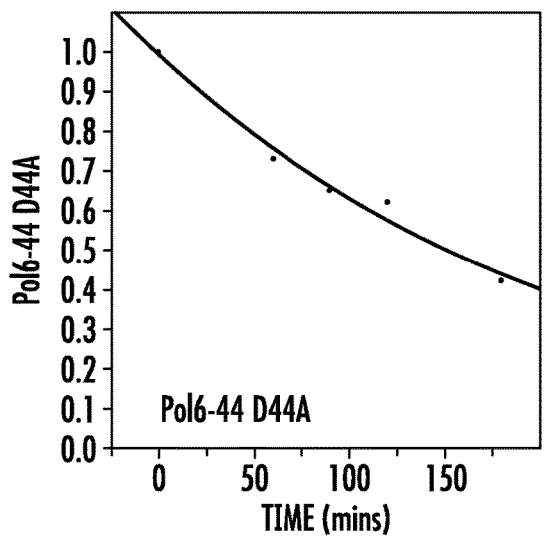
FIG. 3A-D is a graph showing representative data from a static displacement assay for a parental Pol6 polymerase ((A); Pol6-44-D44A; SEQ ID NO:4), and variant Pol6 polymerases Pol6-44-D44A-E585K ((B); SEQ ID NO:6); Pol6-44-A44D-E585K+L731k ((C); SEQ ID NO:7); and Pol6-44-A44D-E585K+M738k ((D); SEQ ID NO:8). Reference is made to Example 3.
Figure 3B:
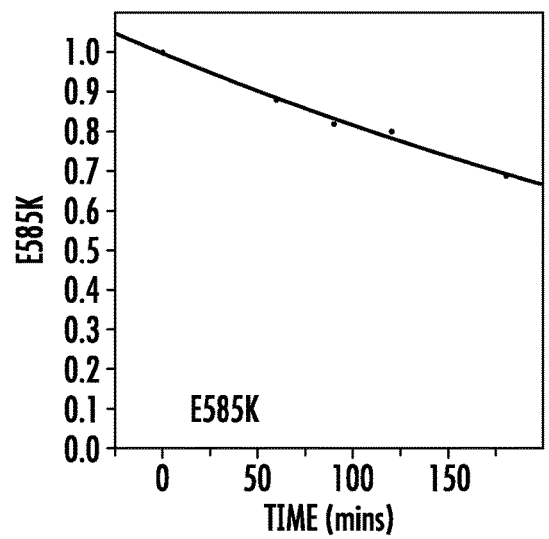
Figure 3C:
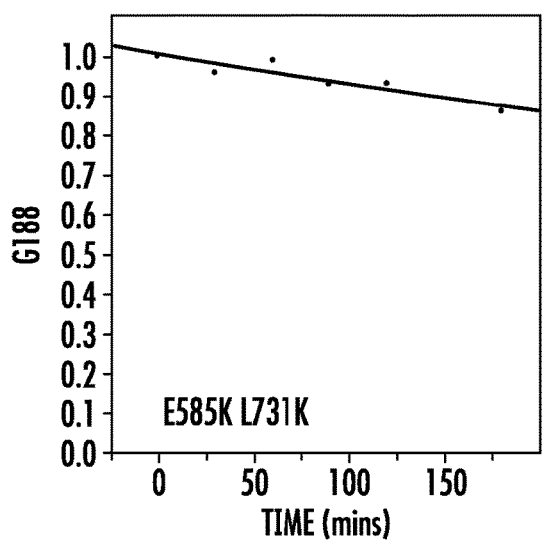
Figure 3D:
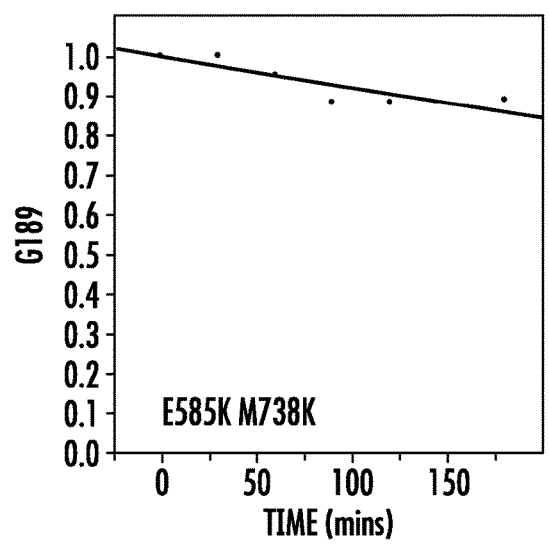

The assay is a FRET assay whereby fluorescence emitted by a fluorogenic DNA template substrate is measured in the presence of non-fluorogenic competing DNA template. Referring to FIG. 2, the FRET assay uses a fluorogenic DNA template comprising Cy5 fluorophore-labelled DNA template (5'-/Cy5/AGA GTG ATA GTA TGA TTA TGT AGA TGT AGG ATT TGA TAT GTG AGT AGC CGA ATG AAA CCT T/iSpC3/TT GGT TTC ATT CGG-3') (SEQ ID NOS: 12 and 16)), and having bound to it a complementary oligonucleotide comprising a quencher 3BHQ-2 (5'-TTT TCA TAA TCA TAC TAT CAC TCT/3BHQ_2/-3' (SEQ ID NO:13)). A DNA polymerase is incubated with the template-oligonucleotide to form a polymerase-template-oligonucleotide complex The rate of dissociation of the variant polymerase form the template-oligonucleotide complex is measured over as the variant polymerase is displaced over time by a competing non-fluorogenic DNA template JAM1G. The amount of undisplaced polymerase-template-oligonucleotide complex is then determined by extending the hairpin template, and measuring the level of fluorescence as the oligonucleotide is displaced.

An assay buffer comprising 208.3 mM HEPES pH7.5, 75 mMKglu, 3.0 mM EDTA, 0.4% Triton X-100, 41.7 mM TCEP, 208.3 µ/ml BSA, and 750 nM hairpin Cy5-labeled DNA template, was used to prepare a working stock of Reagent A.

Three to five microliters of polymerase variant were mixed with twenty-one microliters of Reagent A (Reagent A:Pol variant=3:5), and incubated for 30 minutes at room temperature to allow for the formation of polymerase-DNA template/oligonucleotide complexes.

Following the incubation, 8 µl of the solution comprising the polymerase-DNA template/oligonucleotide complexes were added to each of the wells of a 96-well costar half-area plate.

Seventeen microliters of a stock solution of "Salt & Chase" reagent comprising competing DNA template (488 mM KGlu, and 2.7 mM chaser DNA template JamG1) were added to each of the wells containing the polymerase-DNA/oligonucleotide template mix. The mixture was placed in a plate reader BMG polarstar (BMG Labtech, Cary, N.C.).

Twenty microliters of Reagent B (25 mM HepES pH7.5, 500 mM K-glu, 0.05% Triton-X 100, 5 mM TCEP, 25 ug/ul BSA, 20 uM dN6P, and 5 mM MgCl2) were added to the complexes in the wells to initiate the extension of the DNA template, and the resulting fluorescence was measured at time=0, 30 minutes, 60 minutes, 90 minutes, 120 minutes and 180 minutes.

Baseline fluorescence value was subtracted from all values, and the percent amplitude calculated, where the maximum amplitude at Time T=0 is 100% amplitude at Time T=30 mins Amplitude=(Amp@T=30/Amp@T=0)%. The rate of dissociation was then calculated as the slope of the curve. The results are provided in Table 1 below.

TABLE 1

| Mutants | Template dissociation rate (min-1, 500 mM K-glu) | Fold difference |
|---|---|---|
| (A) Pol6-44 D44A (SEQ ID NO: 4) | −0.00456 | 1.0 |
| (B) Pol 6-44 D44A E585K (SEQ ID NO: 6) | −0.00201 | 2.3 |
| (C) Pol-6-44-D44A_E585K + L731K (SEQ ID NO: 7) | −0.00077 | 5.9 |
| (D) Pol-6-44-D44A_E585K + M738K (SEQ ID NO: 8) | −0.00084 | 5.4 |

The dissociation curves for parental Pol6-44-X1 polymerase, and variants thereof; Pol6-44-X1-E585K, Pol6-44-X1-E585K-L731K and Pol6-44-X1-E585K-M738K, are shown in FIGS. 3A, 3B, 3C and 3D, respectively.

The data show that variant polymerase Pol6 comprising mutations that substitute one or more amino acids of the DNA binding site with a positively charged amino acid e.g. lysine (K), display a decrease in the rate of dissociation from the DNA template, and therefore increased processivity. Accordingly, these variant polymerases are also expected to have increased sequencing life time, and to increase the length of the reads during sequencing events.

Example 4

Attachment to Nanopore

This example provides methods of attaching a variant polymerase to a nanopore, e.g., α-hemolysin; OmpG.

The pol6 variant SpyCatcher HisTag (SEQ ID NO:4) was expressed according to Example 2 and purified using a cobalt affinity column. The SpyCatcher polymerase and a SpyTag-nanopore protein are incubated overnight at 4° C. In 3 mM $SrCl_2$ to form the polymerase-nanopore complex. The polymerase-template complex is formed, purified, and attached to a nanopore to form nano ore sequencing complexes. Methods for preparing and purifying polymerase-template complexes are described in U.S. Provisional application "Purification of Polymerase Complexes" 62/260,194 filed on Nov. 25, 2015, which is herein incorporated by reference in its entirety. Nanopore sequencing complexes can be formed by sequential binding of variant polymerase to nanopore to form an enzyme—nanopore complex, followed by association of template to form the nanopore sequencing complex,. Alternatively, nanopore sequencing complexes can be formed by first associating the template with the variant polymerase to form a template-enzyme complex, and subsequently attaching the template-enzyme complex to the nanopore. Methods for forming nanopore sequencing complexes are described in U.S. Provisional Application 62/281,719 filed on Jan. 21, 2016, which is herein incorporated by reference in its entirety.

A polymerase can be coupled to the nanopore by any suitable means. See, for example, PCT/US2013/068967 (published as WO2014/074727; Genia Technologies, Inc.), PCT/US2005/009702 (published as WO2006/028508; President and Fellows of Harvard College), and PCT/US2011/065640 (published as WO2012/083249; Columbia University).

A variant pol6 DNA polymerase, is coupled to a protein nanopore (e.g., alpha-hemolysin, OmpG), through a linker molecule. Specifically, the SpyTag and SpyCatcher system that spontaneously forms covalent isopeptide linkages under physiological conditions is used. See, for example, Li et al., J Mol Biol. 2014 Jan. 23; 426(2):309-17.

Example 5

Nanopore Sequencing

The ability of a nanopore-bound variant Pol6 polymerase to bind tagged nucleotides and thereby allow for the detection of blocked channel currents at the nanopore to which the polymerase is attached, was determined. Increased processivity of the variant Pol6 polymerases was compared to that of the parent Pol6 lacking the modifications of the variant enzyme.

The variant Pol6 polymerase is collected with DNA template to form variant Pol6-DNA complex, which is subsequently attached to a nanopore embedded in a lipid bilayer over a well on a semiconductor sensor chip, also called a biochip. The lipid bilayer is formed and the nanopore with attached variant Pol6 polymerase-DNA complex i.e. the variant Pol6 nanopore sequencing complex, is inserted as described in PCT/US2014/061853 (entitled "Methods for Forming Lipid Bilayers on Biochips" and filed 22 Oct. 2014).

Alternatively, the nanopore is embedded into the lipid bilayer, and the variant Pol6-DNA complex is attached in situ.

A mixture of tagged nucleotides, where the tag is a polymer of 30 thymine nucleotides (T30) consisting of 3 uM T-T30, 3 uM C-T30, 3 uM G-T30, and 3 uM A-T30, in static conditions (500 mM KGlu, 3 mM $CaCl_2$, 20 mM HEPES, pH8.0), is flowed over the nanopores at a rate of 0.834 ul/second.

An alternating current of 210 mV peak to peak is applied at 25 Hz, and capture nucleotide tags is assessed as nucleotide bases are incorporated into the copied DNA strand by the nanopore-bound polymerase.

Processivity of the variant Pol6 is compared to that of the unmodified parental Pol6 to determine an increase in read-length, and/or speed of polynucleotide synthesis, and/or a decrease in se sequencing error.

SEQUENCE LISTING FREE TEXT

SEQ ID NO: 1 - Wild-type Pol6 (DNA polymerase [Clostridum phage phiCPV4]; GenBank: AFH27113.1)
```
001 mdkhtqyvke hsfnydeykk anfdkiecli fdtesctnye ndntgarvyg wglgvtmhn
061 miygqninqf wevcqnifnd wyhdnkhtik itktkkgfpk rkyikfpiav hnlgwdvefi
121 kyslvengfn ydkgllktvf skgapyqtvt dveepktfhi vqnnnivygc nvymdkffev
181 enkdgsttei glcldffdsy kiitcaesqf hnyvhdvdpm fykmgeeydy dtwrspthkq
241 ttlelryqyn diymlrevie qfyidglcgg elpltgmrta ssiafnvlkk mtfgeektee
301 gyinyfeldk ktkfeflrkr iemesytggy thanhkavgk tinkigcsid inssypsqma
361 ykvfpygkpv rktwgrkpkt eknevyliev gfdfvepkhe eyaldifkig avnskaispi
421 tgavsgqeyf ctnikdgkai pvykelkdtk lttnynvvlt sveyefwikh fnfgvfkkde
481 ydcfevdnle ftglkigsil yykaekgkfk pyvdhftkmk venkklgnkp ltnqakliln
```

```
541 gaygkfgtkq nkeekdlimd knglltftgs vteyegkefy rpyasfvtay grlqlwnaii
601 yavgvenfly cdtdsiycnr evnsliedmn aigetidkti lgkwdvehvf dkfkvlgqkk
661 ymyhdckedk tdlkccglps darkiiigqg fdefylgknv egkkqrkkvi ggcllldtlf
721 tikkimf*
```

SEQ ID NO: 2 - Pol6 (with His tag)

```
MHHHHHHHHS GGSDKHTQYV KEHSFNYDEY KKANFDKIEC LIFDTESCTN          50
YENDNTGARV YGWGLGVTRN HNMIYGQNLN QFWEVCQNIF NDWYHDNKHT         100
IKITKTKKGF PKRKYIKFPI AVHNLGWDVE FLKYSLVENG FNYDKGLLKT         150
VFSKGAPYQT VTDVEEPKTF HIVQNNNIVY GCNVYMDKFF EVENKDGSTT         200
EIGLCLDFFD SYKLITCAES QFHNYVHDVD PMFYKMGEEY DYDTWRSPTH         250
KQTTLELRYQ YNDIYMLREV IEQFYIDGLC GGELPLTGMR TASSIAFNVL         300
KKMTFGEEKT EEGYINYFEL DKKTKFEFLR KRIEMESYTG GYTHANHKAV         350
GKTINKIGCS LDINSSYPSQ MAYKVFPYGK PVRKTWGRKP KTEKNEVYLI         400
EVGFDFVEPK HEEYALDIFK IGAVNSKALS PITGAVSGQE YFCTNIKDGK         450
AIPVYKELKD TKLTTNYNVV LTSVEYEFWI KHFNFGVFKK DEYDCFEVDN         500
LEFTGLKIGS ILYYKAEKGK FKPYVDHFTK MKVENKKLGN KPLTNQAKLI         550
LNGAYGKFGT KQNKEEKDLI MDKNGLLTFT GSVTEYEGKE FYRPYASFVT         600
AYGRLQLWNA IIYAVGVENF LYCDTDSIYC NREVNSLIED MNAIGETIDK         650
TILGKWDVEH VFDKFKVLGQ KKYMYHDCKE DKTDLKCCGL PSDARKIIIG         700
QGFDEFYLGK NVEGKKQRKK VIGGCLLLDT LFTIKKIMF*                    739
```

SEQ ID NO: 3 - Pol6 with His tag (DNA sequence)

```
ATGCATCACC ATCATCATCA CCACCACAGC GGCGGTTCCG ACAAACACAC           50
GCAGTACGTC AAAGAGCATA GCTTCAATTA TGACGAGTAT AAGAAAGCGA          100
ATTTCGACAA GATCGAGTGC CTGATCTTTG ACACCGAGAG CTGCACGAAT          150
TATGAGAACG ATAATACCGG TGCACGTGTT TACGGTTGGG GTCTTGGCGT          200
CACCCGCAAC CACAATATGA TCTACGGCCA AAATCTGAAT CAGTTTTGGG          250
AAGTATGCCA GAACATTTTC AATGATTGGT ATCACGACAA CAAACATACC          300
ATTAAGATTA CCAAGACCAA GAAAGGCTTC CCGAAACGTA AGTACATTAA          350
GTTTCCGATT GCAGTTCACA ATTTGGGCTG GGATGTTGAA TTCCTGAAGT          400
ATAGCCTGGT GGAGAATGGT TTCAATTACG ACAAGGGTCT GCTGAAAACT          450
GTTTTTAGCA AGGGTGCGCC GTACCAAACC GTGACCGATG TTGAGGAACC          500
GAAAACGTTC CATATCGTCC AGAATAACAA CATCGTTTAT GGTTGTAACG          550
TGTATATGGA CAAATTCTTT GAGGTCGAGA ACAAAGACGG CTCTACCACC          600
GAGATTGGCC TGTGCTTGGA TTTCTTCGAT AGCTATAAGA TCATCACGTG          650
TGCTGAGACG CAGTTCCACA ATTACGTTCA TGATGTGGAT CCAATGTTCT          700
ACAAAATGGG TGAAGAGTAT GATTACGATA CTTGGCGTAG CCCGACGCAC          750
AAGCAGACCA CCCTGGAGCT GCGCTACCAA TACAATGATA TCTATATGCT          800
GCGTGAAGTC ATCGAACAGT TTTACATTGA CGGTTTATGT GGCGGCGAGC          850
TGCCGCTGAC CGGCATGCGC ACCGCTTCCA GCATTGCGTT CAACGTGCTG          900
AAAAAGATGA CCTTTGGTGA GGAAAAGACG GAAGAGGGCT ACATCAACTA          950
TTTTGAATTG GAGAAGAAAA CCAAATTCGA GTTTCTGCGT AAGCGCATTG         1000
AAATGGAATC GTACACCGGT GGCTATACGC ACGCAAATCA CAAAGCCGTT         1050
GGTAAGACTA TTAACAAGAT CGGTTGCTCT TTGGACATTA ACAGCTCATA         1100
CCCTTCGCAG ATGGCGTACA AGGTCTTTCC GTATGGCAAA CCGGTTCGTA         1150
AGACCTGGGG TCGTAAACCA AAGACCGAGA AGAACGAAGT TTATCTGATT         1200
GAAGTTGGCT TTGACTTCGT GGAGCCGAAA CACGAAGAAT ACGCGCTGGA         1250
TATCTTTAAG ATTGGTGCGG TGAACTCTAA AGCGCTGAGC CCGATCACCG         1300
GCGCTGTCAG CGGTCAAGAG TATTTCTGTA CGAACATTAA AGACGGCAAA         1350
GCAATCCCGG TTTACAAAGA ACTGAAGGAC ACCAAATTGA CCACTAACTA         1400
CAATGTCGTG CTGACCAGCG TGGAGTACGA GTTCTGGATC AAACACTTCA         1450
ATTTTGGTGT GTTTAAGAAA GACGAGTACG ACTGTTTCGA AGTTGACAAT         1500
CTGGAGTTTA CGGGTCTGAA GATTGGTTCC ATTCTGTACT ACAAGGCAGA         1550
GAAAGGCAAG TTTAAACCTT ACGTGGATCA CTTCACGAAA ATGAAAGTGG         1600
AGAACAAGAA ACTGGGTAAT AAGCCGCTGA CCAATCAGGC AAAGCTGATT         1650
CTGAACGGTG CGTACGGCAA ATTCGGCACC AAACAAAACA AGAAGAGAAA         1700
AGATTTGATC ATGGATAAGA ACGGTTTGCT GACCTTCACG GGTAGCGTCA         1750
CGGAATACGA GGGTAAAGAA TTCTATCGTC CGTATGCGAG CTTCGTTACT         1800
GCCTATGGTC GCCTGCAACT GTGGAACGCG ATTATCTACG CGGTTGGTGT         1850
GGAGAATTTT CTGTACTGCG ACACCGACAG CATCTATTGT AACCGTGAAG         1900
TTAACAGCCT CATTGAGGAT ATGAACGCCA TTGGTGAAAC CATCGATAAA         1950
ACGATTCTGG GTAAATGGGA CGTGGAGCAT GTCTTTGATA AGTTTAAGGT         2000
CCTGGGCCAG AAGAAGTACA TGTATCATGA TTGCAAAGAA GATAAAACGG         2050
ACCTGAAGTG TTGCGGTCTG CCGAGCGATG CCCGTAAGAT TATCATTGGT         2100
CAAGGTTTCG ACGAGTTTTA TCTGGGCAAA AATGTGGAAG GTAAGAAGCA         2150
ACGCAAAAAA GTGATCGGCG GTTGCCTGCT GCTGGACACC CTGTTTACGA         2200
TCAAGAAAAT CATGTTCTAA                                         2220
```

SEQ ID NO: 4 - Pol6-44-.X1 with His-tag/SpyCatcher

```
MHHHHHHHHS GDYDIPTTEN LYFQGAMVDT LSGLSSEQGQ SGDMTIEEDS           50
ATHIKFSKRD EDGKELAGAT MELRDSSGKT ISTWISDGQV KDFYLYPGKY          100
TFVETAAPDG YEVATAITFT VNEQGQVTVN GKATKGDAHI GGSDKHTQYV          150
KEHSFNYDEY KKANFDKIEC LIFATESCTN YENDNTGARV YGWGLGVTRN          200
```

| SEQUENCE LISTING FREE TEXT | |
|---|---|
| HMMIYGQNLN QFWEVCQNIF NDWYHDNKHT IKITKTKKGF PKRKYIKFPI | 250 |
| AVHNLGWDVE FLKYSLVENG FNYDKGLLKT VFSKGAPYQT VTDVEEPKTF | 300 |
| HIVQNNNIVY GCNVYMDKFF EVENKDGSTT EIGLCLDFFD SYKIITCAES | 350 |
| QFHNYVHDVD PMFYKMGEEY DYDTWRSPTH KQTTLELRYQ YNDIYMLREV | 400 |
| IEQFYIDGLC GGELPLTGMR TASSIAFNVL KKMTFGEEKT EEGYINYFEL | 450 |
| DKKTKFEFLR KRIEMESYTG GYTHANHKAV GKTINKIGCS LDINSAYPSQ | 500 |
| MAYKVFPYGK PVRKTWGRKP KTEKNEVYLI EVGFDFVEPK HEEYALDIFK | 550 |
| IGAVNSKALS PITGAVSGQE YFCTNIKDGK AIPVYKELKD TKLTTNYNVV | 600 |
| LTSVEYEFWI KHFNFGVFKK DEYDCFEVDN LEFTGLKIGS ILYYKAEKGK | 650 |
| FKPYVDHFMK MKVENKKLGN KPLTNQFKLI LNGAYGKFGT KQNKEEKDLI | 700 |
| MDKNGLLTFT GSVTEYEGKE FYRPYASFVT AYGRLQLWNA IIYAVGVENF | 750 |
| LYCDTDSIYC NREVNSLIED MNAIGETIDK TILGKWDVEH VFDKFKVLGQ | 800 |
| KKYMHDCKE DKTDLKCCGL PSDARKIIIG QGFDEFYLGK NVEGKKQRKK | 850 |
| VIGGCLLLDT LFTIKKIMF* | 869 |

SEQ ID NO: 5 - PoL6-44-X1 with His-tag/SpyCatcher (DNA sequence)
| ATGCATCACC ATCATCATCA CCACCACAGC GGTGACTACG ACATCCCGAC | 50 |
|---|---|
| CACCGAGAAC CTGTACTTCC AGGGCGCCAT GGTGGACACA CTGAGCGGTC | 100 |
| TGAGCAGTGA ACAGGGCCAG AGCGGCGACA TGACCATTGA AGAGGACAGC | 150 |
| GCCACCCACA TCAAGTTCAG CAAGCGTGAC GAGGACGGTA AGGAACTGGC | 200 |
| CGGCGCCACC ATGGAACTGC GTGACAGCAG CGGCAAGACC ATCAGCACCT | 250 |
| GGATCAGCGA TGGCCAGGTG AAGGACTTCT ACCTGTACCC GGGCAAGTAC | 300 |
| ACCTTCGTGG AGACAGCCGC ACCGGACGGT TACGAGGTTG CCACCGCCAT | 350 |
| CACCTTCACC GTGAACGAGC AGGGCCAAGT GACCGTTAAC GGCAAGGCCA | 400 |
| CCAAGGGTGA CGCCCACATC GGCGGTTCCG ACAAACACAC GCAGTACGTC | 450 |
| AAAGAGCATA GCTTCAATTA TGACGAGTAT AAGAAAGCGA ATTTCGACAA | 500 |
| GATCGAGTGC GTGATCTTTG CGACCGAGAG CTGCACGAAT TATGAGAACG | 550 |
| ATAATACCGG TGCACGTGTT TACGGTTGGG GTCTTGGCGT CACCCGCAAC | 600 |
| CACAATATGA TCTACGGCCA AAATCTGAAT CAGTTTTGGG AAGTATGCCA | 650 |
| GAACATTTTC AATGATTGGT ATCACGACAA CAAACATACC ATTAAGATTA | 700 |
| CCAAGACCAA GAAAGGCTTC CCGAAACGTA AGTACATTAA GTTTCCGATT | 750 |
| GCAGTTCACA ATTTGGGCTG GGATGTTGAA TTCCTGAAGT ATAGCCTGGT | 800 |
| GGAGAATGGT TTCAATTACG ACAAGGGTCT GCTGAAAACT GTTTTTAGCA | 850 |
| AGGGTGCGCC GTACCAAACC GTGACGGATG TTGAGGAACC GAAAACGTTC | 900 |
| CATATCGTCC AGAATAACAA CATCGTTTAT GGTTGTAACG TGTATATGGA | 950 |
| CAAATTCTTT GAGGTCGAGA ACAAAGACGG CTCTACCACC GATTGGCC | 1000 |
| TGTGCTTGGA TTTCTTCGAT AGCTATAAGA TCATCACGTG TGCTGAGAGC | 1050 |
| CAGTTCCACA ATTACGTTCA TGATGTGGAT CCAATGTTCT ACAAAATGGG | 1100 |
| TGAAGAGTAT GATTACGATA CTTGGCGTAG CCCGACGCAC AAGCAGACCA | 1150 |
| CCCTGGAGCT GCGCTACCAA TACAATGATA TCTATATGCT GCGTGAAGTC | 1200 |
| ATCGAACAGT TTTACATTGA CGGTTTATGT GGCGGCAGCG AGCTGCCTGA | 1250 |
| CGGCATGCGC ACCGCTTCCA GCATTGCGTT CAACGTGCTG AAAAAGATGA | 1300 |
| CCTTTGGTGA GGAAAAGACG GAAGAGGGCT ACATCAACTA TTTTGAATTG | 1350 |
| GACAAGAAAA CCAAATTCGA GTTTCTGCGT AAGCGCATTG AAATGGAATC | 1400 |
| GTACACCGGT GGCTATACGC ACGCAAATCA CAAAGCCGTT GGTAAGACTA | 1450 |
| TTAACAAGAT CGGTTGCTCT TTGGACATTA ACGCGCGTA CCCTTCGCAG | 1500 |
| ATGGCGTACA AGGTCTTTCC GTATGGCAAA CCGGTTCGTA AGACCTGGGG | 1550 |
| TCGTAAACCA AAGACCGAGA AGAACGAAGT TTATCTGATT GAAGTTGGCT | 1600 |
| TTGACTTCGT GGAGCCGAAA CACGAAGAAT ACGCGCTGGA TATCTTTAAG | 1650 |
| ATTGGTGCGG TGAACTCTAA AGCGCTGAGC CCGATCACCG GCGCTGTCAG | 1700 |
| CGGTCAAGAG TATTTCTGTA CGAACATTAA AGACGGCAAA GCAATCCCGG | 1750 |
| TTTACAAAGA ACTGAAGGAC ACCAAATTGA CCACTAACTA CAATGTCGTG | 1800 |
| CTGACCAGCG TGGAGTACGA GTTCTGGATC AAACACTTCA ATTTTGGTGT | 1850 |
| GTTTAAGAAA GACGAGTACG ACTGTTTCGA AGTTGACAAT CTGGAGTTTA | 1900 |
| CGGGTCTGAA GATTGGTTCC ATTCTGTACT ACAAGGCAGA GAAAGGCAAG | 1950 |
| TTTAAACCTT ACGTGGATCA CTTCATGAAA ATGAAAGTGG AGAACAAGAA | 2000 |
| ACTGGGTAAT AAGCCGCTGA CGAATCAGTT TAAGCTGATT CTGAACGGTG | 2050 |
| CGTACGGCAA ATTCGGCACC AAACAAAACA AAGAAGAGAA AGATTTGATC | 2100 |
| ATGGATAAGA ACGTTTGCT GACCTTCACG GGTAGCGTCA CGGAATACGA | 2150 |
| GGGTAAAGAA TTCTATCGTC CGTATGCGAG CTTCGTTACT GCCTATGGTC | 2200 |
| GCCTGCAACT GTGGAACGCG ATTATCTACG CGGTTGGTGT GGAGAATTTT | 2250 |
| CTGTACTGCG ACACCGACAG CATCTATTGT AACCGTGAAG TTAACAGCCT | 2300 |
| CATTGAGGAT ATGAACGCCA TTGGTGAAAC CATCGATAAA ACGATTCTGG | 2350 |
| GTAAATGGGA CGTGGAGCAT GTCTTTGATA AGTTTAAGGT CCTGGGCCAG | 2400 |
| AAGAAGTACA TGTATCATGA TTGCAAAGAA GATAAAACGG ACCTGAAGTG | 2450 |
| TTGCGGTCTG CCGAGCGATG CCCGTAAGAT TATCATTGGT CAAGGTTTCG | 2500 |
| ACGAGTTTTA TCTGGGCAAA AATGTCGAAG GTAAGAAGCA ACGCAAAAAA | 2550 |
| GTGATCGGCG GTTGCCTGCT GCTGGACACC CTGTTTACGA TCAAGAAAAT | 2600 |
| CATGTTCTAA | 2610 |

SEQ ID NO: 6 - Pol6-44-XI with His-tag/SpyCatcher +
E585K of SEQ ID NO: 2,
which corresponds to E715K of SEQ ID NO: 6
| MHHHHHHHHS GDYDIPTTEN LYFQGAMVDT LSGLSSEQGQ SGDMTIEEDS | 50 |
|---|---|
| ATHIKFSKRD EDGKELAGAT MELRDSSGKT ISTWISDGQV KDFYLYPGKY | 100 |
| TFVETAAPDG YEVATAITFT VNEQGQVTVN GKATKGDAHI GGSDKHTQYV | 150 |
| KEHSFNYDEY KKANFDKIEC LIFATESCTN YENDNTGARV YGWGLGVTRN | 200 |
| HNMIYGQNLN QFWEVCQNIF NDWYHDNKHT IKITKTKKGF PKRKYIKFPI | 250 |

SEQUENCE LISTING FREE TEXT

```
AVHNLGWDVE FLKYSLVENG FNYDKGLLKT VFSKGAPYQT VTDVEEPKTF       300
HIVQNNNIVY GCNVYMDKFF EVENKDGSTT EIGLCLDFFD SYKIITCAES       350
QFHNYVHDVD PMFYKMGEEY DYDTWRSPTH KQTTLELRYQ YNDIYMLREV       400
IEQFYIDGLC GGELPLTGMR TASSIAFNVL KKMTFGEEKT EEGYINYFEL       450
DKKTKFEFLR KRIEMESYTG GYTHANHKAV GKTINKIGCS LDINSAYPSQ       500
MAYKVFPYGK PVRKTWGRKP KTEKVEVYLI EVGFDFVEPK HEEYALDIFK       550
IGAVNSKALS PITGAVSGQE YFCTNIKDGK AIPVYKELKD TKLTTNYNVV       600
LTSVEYEFWI KHFNFGVFKK DEYDCFEVDN LEFTGLKIGS ILYYKAEKGK       650
FKPYVDHFMK MKVENKKLGN KPLTNQFKLI LNGAYGKFGT KQNKEEKDLI       700
MDKNGLLTFT GSVTKYEGKE FYRPYASFVT AYGRLQLWNA IIYAVGVENF       750
LYCDTDSIYC NREVNSLIED MNAIGETIDK TILGKWDVEH VFDKFKVLGQ       800
KKYMYHDCKE DKTDLKCCGL PSDARKIIIG QGFDEFYLGK NVEGKKQRKK       850
VIGGCLLLDT LFTIKKIMF*                                        869

SEQ ID NO: 7 Pol6-44-X1 with His-tag/SpyCatcher + E585K + L731K of SEQ
ID NO: 2, which correspond to E715K + L861K of SEQ ID NO: 6
MHHHHHHHHS GDYDIPTTEN LYFQGAMVDT LSGLSSEQGQ SGDMTIEEDS        50
ATHIKFSKRD EDGKELAGAT MELRDSSGKT ISTWISDGQV KDFYLYPGKY       100
TFVETAAPDG YEVATAITFT VNEQGQVTVN GKATKGDAHI GGSDKHTQYV       150
KEHSFNYDEY KKANFDKIEC LIFATESCTN YENDNTGARV YGWGLGVTRN       200
HNMIYGQNLN QFWEVCQNIF NDWYHDNKHT IKITKTKKGF PKRKYIKFPI       250
AVHNLGWDVE FLKYSLVENG FNYDKGLLKT VFSKGAPYQT VTDVEEPKTF       300
HIVQNNNIVY GCNVYMDKFF EVENKDGSTT EIGLCLDFFD SYKIITCAES       350
QFHNYVHDVD PMFYKMGEEY DYDTWRSPTH KQTTLELRYQ YNDIYMLREV       400
IEQFYIDGLC GGELPLTGMR TASSIAFNVL KKMTFGEEKT EEGYINYFEL       450
DKKTKFEFLR KRIEMESYTG GYTHANHKAV GKTINKIGCS LDINSAYPSQ       500
MAYKVFPYGK PVRKTWGRKP KTEKNEVYLI EVGFDFVEPK HEEYALDIFK       550
IGAVNSKALS PITGAVSGQE YFCTNIKDGK AIPVYKELKD TKLTTNYNVV       600
LTSVEYEFWI KHFNFGVFKK DEYDCFEVDN LEFTGLKIGS ILYYKAEKGK       650
FKPYVDHFMK MKVENKKLGN KPLTNQFKLI LNGAYGKFGT KQNKEEKDLI       700
MDKNGLLTFT GSVTKYEGKE FYRPYASFVT AYGRLQLWNA IIYAVGVENF       750
LYCDTDSIYC NREVNSLIED MNAIGETIDK TILGKWDVEH VFDKFKVLGQ       800
KKYMYHDCKE DKTDLKCCGL PSDARKIIIG QGFDEFYLGK NVEGKKQRKK       850
VIGGCLLLDT KFTIKKIMF*                                        869

SEQ ID NO: 8 - Pol6-44-X1 with His-tag/SpyCatcher + E585K + M738K of SEQ
ID NO: 2, which correspond to E715K + M868K of SEQ ID NO: 6
MHHHHHHHHS GDYDIPTTEN LYFQGAMVDT LSGLSSEQGQ SGDMTIEEDS        50
ATHIKFSKRD EDGKELAGAT MELRDSSGKT ISTWISDGQV KDFYLYPGKY       100
TFVETAAPDG YEVATAITFT VNEQGQVTVN GKATKGDAHI GGSDKHTQYV       150
KEHSFNYDEY KKANFDKIEC LIFATESCTN YENDNTGARV YGWGLGVTRN       200
HNMIYGQNLN QFWEVCQNIF NDWYHDNKHT IKITKTKKGF PKRKYIKFPI       250
AVHNLGWDVE FLKYSLVENG FNYDKGLLKT VFSKGAPYQT VTDVEEPKTF       300
HIVQNNNIVY GCNVYMDKFF EVENKDGSTT EIGLCLDFFD SYKIITCAES       350
QFHNYVHDVD PMFYKMGEEY DYDTWRSPTH KQTTLELRYQ YNDIYMLREV       400
IEQFYIDGLC GGELPLTGMR TASSIAFNVL KKMTFGEEKT EEGYINYFEL       450
DKKTKFEFLR KRIEMESYTG GYTHANHKAV GKTINKIGCS LDINSAYPSQ       500
MAYKVFPYGK PVRKTWGRKP KTEKNEVYLI EVGFDFVEPK HEEYALDIFK       550
IGAVNSKALS PITGAVSGQE YFCTNIKDGK AIPVYKELKD TKLTTNYNVV       600
LTSVEYEFWI KHFNFGVFKK DEYDCFEVDN LEFTGLKIGS ILYYKAEKGK       650
FKPYVDHFMK MKVENKKLGN KPLTNQFKLI LNGAYGKFGT KQNKEEKDLI       700
MDKNGLLTFT GSVTKYEGKE FYRPYASFVT AYGRLQLWNA IIYAVGVENF       750
LYCDTDSIYC NREVNSLIED MNAIGETIDK TILGKWDVEH VFDKFKVLGQ       800
KKYMYHDCKE DKTDLKCCGL PSDARKIIIG QGFDEFYLGK NVEGKKQRKK       850
VIGGCLLLDT LFTIKKIKF*                                        869

SEQ ID NO: 9 - His 6 tag
HHHHHH

SEQ ID NO: 10 - SpyCatcher
SGDYDIPTTENLYFQGAMVDTLSGLSSEQGQSGDMTIEEDSATHIKFSKRDEDGKELAGATME
LRDSSGKTISTWISDGQVKDFYLYPGKYTFVETAAPDGYEVATAITFTVNEQGQVTVNGKATK
GDAHI SEQ ID NO: 11 - SpyTag
AHIVMVDAYKPTK SEQ ID NOS: 12 and 16 - Cy5-labelled fluorogenic DNA template
Cy5/
AGA GTG ATA GTA TGA TTA TGT AGA TGT AGG ATT TGA TAT GTG AGT AGC
CGA ATGAAA CCT T/iSpC3/TT GGT TTC ATT CGG SEQ ID NO: 13 - Black Hole Quencher® dye-labelled quencher oligonucle-
otide
TTT TCA TAA TCA TAC TAT CAC TCT /3BHQ_2
```

What is claimed is:

1. A variant-polypeptide capable of catalyzing polymerization of deoxynucleotides said polypeptide comprising an amino acid sequence having at least 95% sequence identity with SEQ ID NO: 2, wherein the amino sequence comprises an E585K/R/H substitution relative to SEQ ID NO: 2.

2. The polypeptide of claim 1, further comprising a member of an attachment selected from the group (a) a Spycatcher/SpyTag peptide system, (b) a native chemical ligation system, (c) a sortase system, (d) a transglutaminase systems, (e) a formylglycine linkage system, (f) a system comprising reaction between 6-hydrazino-nicotinic acid and 4-formylbenzoate, and (g) a zinc finger system attaching the polypeptide to a biological nanopore.

3. The polypeptide of claim 1, wherein said amino acid sequence further comprises an M738K/R/H substitution relative to SEQ ID NO: 2.

4. The polypeptide of claim 1, wherein said amino acid sequence further comprises a D44A, S366A, T529M, and A547F relative to SEQ ID NO: 2.

5. The polypeptide of claim 2, wherein said amino acid sequence further comprises a D44A, S366A, T529M, and A547F relative to SEQ ID NO: 2.

6. The polypeptide of claim 3, wherein said amino acid sequence further comprises a D44A, S366A, T529M, and A547F relative to SEQ ID NO: 2.

7. The polypeptide of claim 4, wherein said polypeptide has a reduced rate of dissociation in the presence of 500 mM potassium glutamate relative to a polypeptide consisting of SEQ ID NO: 4.

8. The polypeptide of claim 5, wherein said polypeptide has a reduced rate of dissociation in the presence of 500 mM potassium glutamate relative to a polypeptide consisting of SEQ ID NO: 4.

9. The polypeptide of claim 6, wherein said polypeptide has a reduced rate of dissociation in the presence of 500 mM potassium glutamate relative to a polypeptide consisting of SEQ ID NO: 4.

10. The polypeptide of claim 1, wherein the amino acid sequence comprises residues 141-869 of SEQ ID NO: 6, residues 141-869of SEQ ID NO: 7, or residues 141-869 of SEQ ID NO: 8.

11. The polypeptide of claim 1, further comprising an affinity tag.

12. The polypeptide of claim 1, further comprising means for attaching the polypeptide to a biological nanopore.

13. A composition comprising the polypeptide of claim 1 attached to a biological nanopore.

14. The composition of claim 13, wherein the attachment between the polypeptide and the biological nanopore results from an attachment system selected from the group consisting of: (a) a SpyCatcher/SpyTag peptide system, (b) a native chemical ligation system, (c) a sortase system, (d) a transglutaminase systems, (e) a formylglycine linkage system, (f) a system comprising reaction between 6-hydrazino-nicotinic acid and 4-formylbenzoate, and (g) a zinc finger system.

15. The composition of claim 13, further comprising a polynucleotide complexed with the polypeptide.

16. A biochip comprising a plurality of nanopore sequencing complexes, wherein each nanopore sequencing complex comprises:
a nanopore inserted in a membrane adjacent to an electrode of a sensing circuit,
the polypeptide of claim 1 attached to the nanopore, and
a polynucleotide complexed with the polypeptide.

17. The biochip of claim 16, wherein the nanopore is a biological nanopore.

18. The biochip of claim 16, wherein the biochip comprises at least 500 nanopore sequencing complexes per 1 $mm^2$.

* * * * *

SEQUENCE LISTING

<160> NUMBER OF SEQ ID NOS: 16

<210> SEQ ID NO 1
<211> LENGTH: 727
<212> TYPE: PRT
<213> ORGANISM: Clostridium phage phiCPV4

<400> SEQUENCE: 1

```
Met Asp Lys His Thr Gln Tyr Val Lys Glu His Ser Phe Asn Tyr Asp
1               5                   10                  15

Glu Tyr Lys Lys Ala Asn Phe Asp Lys Ile Glu Cys Leu Ile Phe Asp
            20                  25                  30

Thr Glu Ser Cys Thr Asn Tyr Glu Asn Asp Asn Thr Gly Ala Arg Val
        35                  40                  45

Tyr Gly Trp Gly Leu Gly Val Thr Arg Asn His Asn Met Ile Tyr Gly
    50                  55                  60

Gln Asn Leu Asn Gln Phe Trp Glu Val Cys Gln Asn Ile Phe Asn Asp
65                  70                  75                  80

Trp Tyr His Asp Asn Lys His Thr Ile Lys Ile Thr Lys Thr Lys Lys
                85                  90                  95

Gly Phe Pro Lys Arg Lys Tyr Ile Lys Phe Pro Ile Ala Val His Asn
            100                 105                 110

Leu Gly Trp Asp Val Glu Phe Leu Lys Tyr Ser Leu Val Glu Asn Gly
        115                 120                 125

Phe Asn Tyr Asp Lys Gly Leu Leu Lys Thr Val Phe Ser Lys Gly Ala
    130                 135                 140

Pro Tyr Gln Thr Val Thr Asp Val Glu Glu Pro Lys Thr Phe His Ile
145                 150                 155                 160

Val Gln Asn Asn Asn Ile Val Tyr Gly Cys Asn Val Tyr Met Asp Lys
                165                 170                 175

Phe Phe Glu Val Glu Asn Lys Asp Gly Ser Thr Thr Glu Ile Gly Leu
            180                 185                 190

Cys Leu Asp Phe Phe Asp Ser Tyr Lys Ile Ile Thr Cys Ala Glu Ser
        195                 200                 205

Gln Phe His Asn Tyr Val His Asp Val Asp Pro Met Phe Tyr Lys Met
    210                 215                 220

Gly Glu Glu Tyr Asp Tyr Asp Thr Trp Arg Ser Pro Thr His Lys Gln
225                 230                 235                 240

Thr Thr Leu Glu Leu Arg Tyr Gln Tyr Asn Asp Ile Tyr Met Leu Arg
                245                 250                 255

Glu Val Ile Glu Gln Phe Tyr Ile Asp Gly Leu Cys Gly Gly Glu Leu
            260                 265                 270

Pro Leu Thr Gly Met Arg Thr Ala Ser Ser Ile Ala Phe Asn Val Leu
        275                 280                 285

Lys Lys Met Thr Phe Gly Glu Glu Lys Thr Glu Glu Gly Tyr Ile Asn
    290                 295                 300

Tyr Phe Glu Leu Asp Lys Lys Thr Lys Phe Glu Phe Leu Arg Lys Arg
305                 310                 315                 320

Ile Glu Met Glu Ser Tyr Thr Gly Gly Tyr Thr His Ala Asn His Lys
                325                 330                 335

Ala Val Gly Lys Thr Ile Asn Lys Ile Gly Cys Ser Leu Asp Ile Asn
            340                 345                 350

Ser Ser Tyr Pro Ser Gln Met Ala Tyr Lys Val Phe Pro Tyr Gly Lys
        355                 360                 365
```

```
Pro Val Arg Lys Thr Trp Gly Arg Lys Pro Lys Thr Glu Lys Asn Glu
    370                 375                 380

Val Tyr Leu Ile Glu Val Gly Phe Asp Phe Val Glu Pro Lys His Glu
385                 390                 395                 400

Glu Tyr Ala Leu Asp Ile Phe Lys Ile Gly Ala Val Asn Ser Lys Ala
                405                 410                 415

Leu Ser Pro Ile Thr Gly Ala Val Ser Gly Gln Glu Tyr Phe Cys Thr
            420                 425                 430

Asn Ile Lys Asp Gly Lys Ala Ile Pro Val Tyr Lys Glu Leu Lys Asp
        435                 440                 445

Thr Lys Leu Thr Thr Asn Tyr Asn Val Val Leu Thr Ser Val Glu Tyr
    450                 455                 460

Glu Phe Trp Ile Lys His Phe Asn Phe Gly Val Phe Lys Lys Asp Glu
465                 470                 475                 480

Tyr Asp Cys Phe Glu Val Asp Asn Leu Glu Phe Thr Gly Leu Lys Ile
                485                 490                 495

Gly Ser Ile Leu Tyr Tyr Lys Ala Glu Lys Gly Lys Phe Lys Pro Tyr
            500                 505                 510

Val Asp His Phe Thr Lys Met Lys Val Glu Asn Lys Lys Leu Gly Asn
        515                 520                 525

Lys Pro Leu Thr Asn Gln Ala Lys Leu Ile Leu Asn Gly Ala Tyr Gly
    530                 535                 540

Lys Phe Gly Thr Lys Gln Asn Lys Glu Glu Lys Asp Leu Ile Met Asp
545                 550                 555                 560

Lys Asn Gly Leu Leu Thr Phe Thr Gly Ser Val Thr Glu Tyr Glu Gly
                565                 570                 575

Lys Glu Phe Tyr Arg Pro Tyr Ala Ser Phe Val Thr Ala Tyr Gly Arg
            580                 585                 590

Leu Gln Leu Trp Asn Ala Ile Ile Tyr Ala Val Gly Val Glu Asn Phe
        595                 600                 605

Leu Tyr Cys Asp Thr Asp Ser Ile Tyr Cys Asn Arg Glu Val Asn Ser
    610                 615                 620

Leu Ile Glu Asp Met Asn Ala Ile Gly Glu Thr Ile Asp Lys Thr Ile
625                 630                 635                 640

Leu Gly Lys Trp Asp Val Glu His Val Phe Asp Lys Phe Lys Val Leu
                645                 650                 655

Gly Gln Lys Lys Tyr Met Tyr His Asp Cys Lys Glu Asp Lys Thr Asp
            660                 665                 670

Leu Lys Cys Cys Gly Leu Pro Ser Asp Ala Arg Lys Ile Ile Ile Gly
        675                 680                 685

Gln Gly Phe Asp Glu Phe Tyr Leu Gly Lys Asn Val Glu Gly Lys Lys
    690                 695                 700

Gln Arg Lys Lys Val Ile Gly Gly Cys Leu Leu Leu Asp Thr Leu Phe
705                 710                 715                 720

Thr Ile Lys Lys Ile Met Phe
                725

<210> SEQ ID NO 2
<211> LENGTH: 739
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 2

Met His His His His His His Ser Gly Gly Ser Asp Lys His
1               5                   10                  15

Thr Gln Tyr Val Lys Glu His Ser Phe Asn Tyr Asp Glu Tyr Lys Lys
                20                  25                  30

Ala Asn Phe Asp Lys Ile Glu Cys Leu Ile Phe Asp Thr Glu Ser Cys
            35                  40                  45

Thr Asn Tyr Glu Asn Asp Asn Thr Gly Ala Arg Val Tyr Gly Trp Gly
        50                  55                  60

Leu Gly Val Thr Arg Asn His Asn Met Ile Tyr Gly Gln Asn Leu Asn
65                  70                  75                  80

Gln Phe Trp Glu Val Cys Gln Asn Ile Phe Asn Asp Trp Tyr His Asp
                85                  90                  95

Asn Lys His Thr Ile Lys Ile Thr Lys Thr Lys Gly Phe Pro Lys
            100                 105                 110

Arg Lys Tyr Ile Lys Phe Pro Ile Ala Val His Asn Leu Gly Trp Asp
        115                 120                 125

Val Glu Phe Leu Lys Tyr Ser Leu Val Glu Asn Gly Phe Asn Tyr Asp
    130                 135                 140

Lys Gly Leu Leu Lys Thr Val Phe Ser Lys Gly Ala Pro Tyr Gln Thr
145                 150                 155                 160

Val Thr Asp Val Glu Glu Pro Lys Thr Phe His Ile Val Gln Asn Asn
                165                 170                 175

Asn Ile Val Tyr Gly Cys Asn Val Tyr Met Asp Lys Phe Phe Glu Val
            180                 185                 190

Glu Asn Lys Asp Gly Ser Thr Thr Glu Ile Gly Leu Cys Leu Asp Phe
        195                 200                 205

Phe Asp Ser Tyr Lys Ile Ile Thr Cys Ala Glu Ser Gln Phe His Asn
210                 215                 220

Tyr Val His Asp Val Asp Pro Met Phe Tyr Lys Met Gly Glu Glu Tyr
225                 230                 235                 240

Asp Tyr Asp Thr Trp Arg Ser Pro Thr His Lys Gln Thr Thr Leu Glu
                245                 250                 255

Leu Arg Tyr Gln Tyr Asn Asp Ile Tyr Met Leu Arg Glu Val Ile Glu
            260                 265                 270

Gln Phe Tyr Ile Asp Gly Leu Cys Gly Gly Glu Leu Pro Leu Thr Gly
        275                 280                 285

Met Arg Thr Ala Ser Ser Ile Ala Phe Asn Val Leu Lys Lys Met Thr
290                 295                 300

Phe Gly Glu Glu Lys Thr Glu Glu Gly Tyr Ile Asn Tyr Phe Glu Leu
305                 310                 315                 320

Asp Lys Lys Thr Lys Phe Glu Phe Leu Arg Lys Arg Ile Glu Met Glu
                325                 330                 335

Ser Tyr Thr Gly Gly Tyr Thr His Ala Asn His Lys Ala Val Gly Lys
            340                 345                 350

Thr Ile Asn Lys Ile Gly Cys Ser Leu Asp Ile Asn Ser Ser Tyr Pro
        355                 360                 365

Ser Gln Met Ala Tyr Lys Val Phe Pro Tyr Gly Lys Pro Val Arg Lys
370                 375                 380

Thr Trp Gly Arg Lys Pro Lys Thr Glu Lys Asn Glu Val Tyr Leu Ile
385                 390                 395                 400

Glu Val Gly Phe Asp Phe Val Glu Pro Lys His Glu Glu Tyr Ala Leu
                405                 410                 415
```

```
Asp Ile Phe Lys Ile Gly Ala Val Asn Ser Lys Ala Leu Ser Pro Ile
                420                 425                 430
Thr Gly Ala Val Ser Gly Gln Glu Tyr Phe Cys Thr Asn Ile Lys Asp
            435                 440                 445
Gly Lys Ala Ile Pro Val Tyr Lys Glu Leu Lys Asp Thr Lys Leu Thr
        450                 455                 460
Thr Asn Tyr Asn Val Val Leu Thr Ser Val Glu Tyr Glu Phe Trp Ile
465                 470                 475                 480
Lys His Phe Asn Phe Gly Val Phe Lys Lys Asp Glu Tyr Asp Cys Phe
                485                 490                 495
Glu Val Asp Asn Leu Glu Phe Thr Gly Leu Lys Ile Gly Ser Ile Leu
            500                 505                 510
Tyr Tyr Lys Ala Glu Lys Gly Lys Phe Lys Pro Tyr Val Asp His Phe
        515                 520                 525
Thr Lys Met Lys Val Glu Asn Lys Lys Leu Gly Asn Lys Pro Leu Thr
530                 535                 540
Asn Gln Ala Lys Leu Ile Leu Asn Gly Ala Tyr Gly Lys Phe Gly Thr
545                 550                 555                 560
Lys Gln Asn Lys Glu Glu Lys Asp Leu Ile Met Asp Lys Asn Gly Leu
                565                 570                 575
Leu Thr Phe Thr Gly Ser Val Thr Glu Tyr Glu Gly Lys Glu Phe Tyr
            580                 585                 590
Arg Pro Tyr Ala Ser Phe Val Thr Ala Tyr Gly Arg Leu Gln Leu Trp
        595                 600                 605
Asn Ala Ile Ile Tyr Ala Val Gly Val Glu Asn Phe Leu Tyr Cys Asp
610                 615                 620
Thr Asp Ser Ile Tyr Cys Asn Arg Glu Val Asn Ser Leu Ile Glu Asp
625                 630                 635                 640
Met Asn Ala Ile Gly Glu Thr Ile Asp Lys Thr Ile Leu Gly Lys Trp
                645                 650                 655
Asp Val Glu His Val Phe Asp Lys Phe Lys Val Leu Gly Gln Lys Lys
            660                 665                 670
Tyr Met Tyr His Asp Cys Lys Glu Asp Lys Thr Asp Leu Lys Cys Cys
        675                 680                 685
Gly Leu Pro Ser Asp Ala Arg Lys Ile Ile Gly Gln Gly Phe Asp
690                 695                 700
Glu Phe Tyr Leu Gly Lys Asn Val Glu Gly Lys Lys Gln Arg Lys Lys
705                 710                 715                 720
Val Ile Gly Gly Cys Leu Leu Leu Asp Thr Leu Phe Thr Ile Lys Lys
                725                 730                 735
Ile Met Phe

<210> SEQ ID NO 3
<211> LENGTH: 2220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgcatcacc atcatcatca ccaccacagc ggcggttccg acaaacacac gcagtacgtc      60
aaagagcata gcttcaatta tgacgagtat aagaaagcga attcgacaa gatcgagtgc     120 ctgatctttg acaccgagag ctgcacgaat tatgagaacg ataataccgg tgcacgtgtt     180
```

```
tacggttggg gtcttggcgt cacccgcaac cacaatatga tctacggcca aaatctgaat    240
cagttttggg aagtatgcca gaacattttc aatgattggt atcacgacaa caaacatacc    300
attaagatta ccaagaccaa gaaaggcttc ccgaaacgta agtacattaa gtttccgatt    360
gcagttcaca atttgggctg ggatgttgaa ttcctgaagt atagcctggt ggagaatggt    420
ttcaattacg acaagggtct gctgaaaact gttttagca agggtgcgcc gtaccaaacc    480
gtgaccgatg ttgaggaacc gaaaacgttc catatcgtcc agaataacaa catcgtttat    540
ggttgtaacg tgtatatgga caaattcttt gaggtcgaga caaagacgg ctctaccacc    600
gagattggcc tgtgcttgga tttcttcgat agctataaga tcatcacgtg tgctgagagc    660
cagttccaca attacgttca tgatgtggat ccaatgttct acaaaatggg tgaagagtat    720
gattacgata cttggcgtag cccgacgcac aagcagacca ccctggagct gcgctaccaa    780
tacaatgata tctatatgct gcgtgaagtc atcgaacagt tttacattga cggtttatgt    840
ggcggcgagc tgccgctgac cggcatgcgc accgcttcca gcattgcgtt caacgtgctg    900
aaaaagatga cctttggtga ggaaaagacg gaagagggct acatcaacta ttttgaattg    960
gacaagaaaa ccaaattcga gtttctgcgt aagcgcattg aaatggaatc gtacaccggt   1020
ggctatacgc acgcaaatca caaagccgtt ggtaagacta ttaacaagat cggttgctct   1080
ttggacatta acagctcata cccttcgcag atggcgtaca aggtctttcc gtatggcaaa   1140
ccggttcgta agacctgggg tcgtaaacca agaccgaga agaacgaagt ttatctgatt   1200
gaagttggct ttgacttcgt ggagccgaaa cacgaagaat acgcgctgga tatctttaag   1260
attggtgcgg tgaactctaa agcgctgagc ccgatcaccg cgctgtcag cggtcaagag   1320
tatttctgta cgaacattaa agacggcaaa gcaatcccgg tttacaaaga actgaaggac   1380
accaaaattga ccactaacta caatgtcgtg ctgaccagcg tggagtacga gttctggatc   1440
aaacacttca attttggtgt gtttaagaaa gacgagtacg actgtttcga agttgacaat   1500
ctggagtta cgggtctgaa gattggttcc attctgtact acaaggcaga gaaaggcaag   1560
tttaaacctt acgtggatca cttcacgaaa atgaaagtgg agaacaagaa actgggtaat   1620
aagccgctga cgaatcaggc aaagctgatt ctgaacggtg cgtacggcaa attcggcacc   1680
aaacaaaaca agaagagaa agatttgatc atggataaga acggtttgct gaccttcacg   1740
ggtagcgtca cggaatacga gggtaaagaa ttctatcgtc cgtatgcgag cttcgttact   1800
gcctatggtc gcctgcaact gtggaacgcg attatctacg cggttggtgt ggagaatttt   1860
ctgtactgcg acaccgacag catctattgt aaccgtgaag ttaacagcct cattgaggat   1920
atgaacgcca ttggtgaaac catcgataaa acgattctgg gtaaatggga cgtggagcat   1980
gtcttgata agtttaaggt cctgggccag aagaagtaca tgtatcatga ttgcaaagaa   2040
gataaaacgg acctgaagtg ttgcggtctg ccgagcgatg cccgtaagat tatcattggt   2100
caaggtttcg acgagtttta tctgggcaaa aatgtcgaag gtaagaagca acgcaaaaaa   2160
gtgatcggcg gttgcctgct gctggacacc ctgtttacga tcaagaaaat catgttctaa   2220
```

<210> SEQ ID NO 4
<211> LENGTH: 869
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 4

Met His His His His His His His Ser Gly Asp Tyr Asp Ile Pro
1               5                   10                  15

Thr Thr Glu Asn Leu Tyr Phe Gln Gly Ala Met Val Asp Thr Leu Ser
            20                  25                  30

Gly Leu Ser Ser Glu Gln Gly Gln Ser Gly Asp Met Thr Ile Glu Glu
            35                  40                  45

Asp Ser Ala Thr His Ile Lys Phe Ser Lys Arg Asp Glu Asp Gly Lys
50                  55                  60

Glu Leu Ala Gly Ala Thr Met Glu Leu Arg Asp Ser Ser Gly Lys Thr
65                  70                  75                  80

Ile Ser Thr Trp Ile Ser Asp Gly Gln Val Lys Asp Phe Tyr Leu Tyr
                85                  90                  95

Pro Gly Lys Tyr Thr Phe Val Glu Thr Ala Ala Pro Asp Gly Tyr Glu
            100                 105                 110

Val Ala Thr Ala Ile Thr Phe Thr Val Asn Glu Gln Gly Gln Val Thr
            115                 120                 125

Val Asn Gly Lys Ala Thr Lys Gly Asp Ala His Ile Gly Gly Ser Asp
130                 135                 140

Lys His Thr Gln Tyr Val Lys Glu His Ser Phe Asn Tyr Asp Glu Tyr
145                 150                 155                 160

Lys Lys Ala Asn Phe Asp Lys Ile Glu Cys Leu Ile Phe Ala Thr Glu
                165                 170                 175

Ser Cys Thr Asn Tyr Glu Asn Asp Asn Thr Gly Ala Arg Val Tyr Gly
            180                 185                 190

Trp Gly Leu Gly Val Thr Arg Asn His Asn Met Ile Tyr Gly Gln Asn
            195                 200                 205

Leu Asn Gln Phe Trp Glu Val Cys Gln Asn Ile Phe Asn Asp Trp Tyr
210                 215                 220

His Asp Asn Lys His Thr Ile Lys Ile Thr Lys Thr Lys Gly Phe
225                 230                 235                 240

Pro Lys Arg Lys Tyr Ile Lys Phe Pro Ile Ala Val His Asn Leu Gly
                245                 250                 255

Trp Asp Val Glu Phe Leu Lys Tyr Ser Leu Val Glu Asn Gly Phe Asn
            260                 265                 270

Tyr Asp Lys Gly Leu Leu Lys Thr Val Phe Ser Lys Gly Ala Pro Tyr
            275                 280                 285

Gln Thr Val Thr Asp Val Glu Glu Pro Lys Thr Phe His Ile Val Gln
290                 295                 300

Asn Asn Asn Ile Val Tyr Gly Cys Asn Val Tyr Met Asp Lys Phe Phe
305                 310                 315                 320

Glu Val Glu Asn Lys Asp Gly Ser Thr Thr Glu Ile Gly Leu Cys Leu
                325                 330                 335

Asp Phe Phe Asp Ser Tyr Lys Ile Ile Thr Cys Ala Glu Ser Gln Phe
            340                 345                 350

His Asn Tyr Val His Asp Val Asp Pro Met Phe Tyr Lys Met Gly Glu
            355                 360                 365

Glu Tyr Asp Tyr Asp Thr Trp Arg Ser Pro Thr His Lys Gln Thr Thr
370                 375                 380

Leu Glu Leu Arg Tyr Gln Tyr Asn Asp Ile Tyr Met Leu Arg Glu Val
385                 390                 395                 400

Ile Glu Gln Phe Tyr Ile Asp Gly Leu Cys Gly Gly Glu Leu Pro Leu
                405                 410                 415

-continued

```
Thr Gly Met Arg Thr Ala Ser Ser Ile Ala Phe Asn Val Leu Lys Lys
            420                 425                 430

Met Thr Phe Gly Glu Glu Lys Thr Glu Glu Gly Tyr Ile Asn Tyr Phe
        435                 440                 445

Glu Leu Asp Lys Lys Thr Lys Phe Glu Phe Leu Arg Lys Arg Ile Glu
    450                 455                 460

Met Glu Ser Tyr Thr Gly Gly Tyr Thr His Ala Asn His Lys Ala Val
465                 470                 475                 480

Gly Lys Thr Ile Asn Lys Ile Gly Cys Ser Leu Asp Ile Asn Ser Ala
                485                 490                 495

Tyr Pro Ser Gln Met Ala Tyr Lys Val Phe Pro Tyr Gly Lys Pro Val
            500                 505                 510

Arg Lys Thr Trp Gly Arg Lys Pro Lys Thr Glu Lys Asn Glu Val Tyr
        515                 520                 525

Leu Ile Glu Val Gly Phe Asp Phe Val Glu Pro Lys His Glu Glu Tyr
    530                 535                 540

Ala Leu Asp Ile Phe Lys Ile Gly Ala Val Asn Ser Lys Ala Leu Ser
545                 550                 555                 560

Pro Ile Thr Gly Ala Val Ser Gly Gln Glu Tyr Phe Cys Thr Asn Ile
                565                 570                 575

Lys Asp Gly Lys Ala Ile Pro Val Tyr Lys Glu Leu Lys Asp Thr Lys
            580                 585                 590

Leu Thr Thr Asn Tyr Asn Val Val Leu Thr Ser Val Glu Tyr Glu Phe
        595                 600                 605

Trp Ile Lys His Phe Asn Phe Gly Val Phe Lys Lys Asp Glu Tyr Asp
    610                 615                 620

Cys Phe Glu Val Asp Asn Leu Glu Phe Thr Gly Leu Lys Ile Gly Ser
625                 630                 635                 640

Ile Leu Tyr Tyr Lys Ala Glu Lys Gly Lys Phe Lys Pro Tyr Val Asp
                645                 650                 655

His Phe Met Lys Met Lys Val Glu Asn Lys Lys Leu Gly Asn Lys Pro
            660                 665                 670

Leu Thr Asn Gln Phe Lys Leu Ile Leu Asn Gly Ala Tyr Gly Lys Phe
        675                 680                 685

Gly Thr Lys Gln Asn Lys Glu Glu Lys Asp Leu Ile Met Asp Lys Asn
    690                 695                 700

Gly Leu Leu Thr Phe Thr Gly Ser Val Thr Glu Tyr Glu Gly Lys Glu
705                 710                 715                 720

Phe Tyr Arg Pro Tyr Ala Ser Phe Val Thr Ala Tyr Gly Arg Leu Gln
                725                 730                 735

Leu Trp Asn Ala Ile Ile Tyr Ala Val Gly Val Glu Asn Phe Leu Tyr
            740                 745                 750

Cys Asp Thr Asp Ser Ile Tyr Cys Asn Arg Glu Val Asn Ser Leu Ile
        755                 760                 765

Glu Asp Met Asn Ala Ile Gly Glu Thr Ile Asp Lys Thr Ile Leu Gly
    770                 775                 780

Lys Trp Asp Val Glu His Val Phe Asp Lys Phe Lys Val Leu Gly Gln
785                 790                 795                 800

Lys Lys Tyr Met Tyr His Asp Cys Lys Glu Asp Lys Thr Asp Leu Lys
                805                 810                 815

Cys Cys Gly Leu Pro Ser Asp Ala Arg Lys Ile Ile Ile Gly Gln Gly
            820                 825                 830
```

```
Phe Asp Glu Phe Tyr Leu Gly Lys Asn Val Glu Gly Lys Lys Gln Arg
            835                 840                 845

Lys Lys Val Ile Gly Gly Cys Leu Leu Leu Asp Thr Leu Phe Thr Ile
        850                 855                 860

Lys Lys Ile Met Phe
865

<210> SEQ ID NO 5
<211> LENGTH: 2610
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

| | | | | | |
|---|---|---|---|---|---|
| atgcatcacc | atcatcatca | ccaccacagc | ggtgactacg | acatcccgac | caccgagaac | 60 |
| ctgtacttcc | agggcgccat | ggtggacaca | ctgagcggtc | tgagcagtga | acagggccag | 120 |
| agcggcgaca | tgaccattga | agaggacagc | gccacccaca | tcaagttcag | caagcgtgac | 180 |
| gaggacggta | aggaactggc | cggcgccacc | atggaactgc | gtgacagcag | cggcaagacc | 240 |
| atcagcacct | ggatcagcga | tggccaggtg | aaggacttct | acctgtaccc | gggcaagtac | 300 |
| accttcgtgg | agacagccgc | accggacggt | tacgaggttg | ccaccgccat | caccttcacc | 360 |
| gtgaacgagc | agggccaagt | gaccgttaac | ggcaaggcca | ccaagggtga | cgcccacatc | 420 |
| ggcggttccg | acaaacacac | gcagtacgtc | aaagagcata | gcttcaatta | tgacgagtat | 480 |
| aagaaagcga | atttcgacaa | gatcgagtgc | ctgatctttg | cgaccgagag | ctgcacgaat | 540 |
| tatgagaacg | ataataccgg | tgcacgtgtt | tacggttggg | gtcttggcgt | cacccgcaac | 600 |
| cacaatatga | tctacggcca | aaatctgaat | cagttttggg | aagtatgcca | gaacattttc | 660 |
| aatgattggt | atcacgacaa | caaacatacc | attaagatta | ccaagaccaa | gaaaggcttc | 720 |
| ccgaaacgta | agtacattaa | gtttccgatt | gcagttcaca | atttgggctg | gatgttgaa | 780 |
| ttcctgaagt | atagcctggt | ggagaatggt | ttcaattacg | acaagggtct | gctgaaaact | 840 |
| gttttttagca | agggtgcgcc | gtaccaaacc | gtgaccgatg | ttgaggaacc | gaaaacgttc | 900 |
| catatcgtcc | agaataacaa | catcgtttat | ggttgtaacg | tgtatatgga | caaattcttt | 960 |
| gaggtcgaga | caaagacgg | ctctaccacc | gagattggcc | tgtgcttgga | tttcttcgat | 1020 |
| agctataaga | tcatcacgtg | tgctgagagc | cagttccaca | attacgttca | tgatgtggat | 1080 |
| ccaatgttct | acaaaatggg | tgaagagtat | gattacgata | cttggcgtag | cccgacgcac | 1140 |
| aagcagacca | cctggagct | cgctaccaa | tacaatgata | tctatatgct | gcgtgaagtc | 1200 |
| atcgaacagt | tttacattga | cggttttatgt | ggcggcgagc | tgccgctgac | cggcatgcgc | 1260 |
| accgcttcca | gcattgcgtt | caacgtgctg | aaaaagatga | cctttggtga | ggaaaagacg | 1320 |
| gaagagggct | acatcaacta | tttttgaattg | acaagaaaa | ccaaattcga | gtttctgcgt | 1380 |
| aagcgcattg | aaatggaatc | gtacaccggt | ggctatacgc | acgcaaatca | caaagccgtt | 1440 |
| ggtaagacta | ttaacaagat | cggttgctct | ttggacatta | cagcgcgta | cccttcgcag | 1500 |
| atggcgtaca | aggtctttcc | gtatggcaaa | ccggttcgta | agacctgggg | tcgtaaacca | 1560 |
| aagaccgaga | agaacgaagt | ttatctgatt | gaagttggct | ttgacttcgt | ggagccgaaa | 1620 |
| cacgaagaat | acgcgctgga | tatctttaag | attggtgcgg | tgaactctaa | agcgctgagc | 1680 |
| ccgatcaccg | gcgctgtcag | cggtcaagag | tatttctgta | cgaacattaa | agacggcaaa | 1740 |
| gcaatcccgg | tttacaaaga | actgaaggac | accaaattga | ccactaacta | caatgtcgtg | 1800 |

```
ctgaccagcg tggagtacga gttctggatc aaacacttca attttggtgt gtttaagaaa   1860
gacgagtacg actgtttcga agttgacaat ctggagttta cgggtctgaa gattggttcc   1920
attctgtact acaaggcaga gaaaggcaag tttaaacctt acgtggatca cttcatgaaa   1980
atgaaagtgg agaacaagaa actgggtaat aagccgctga cgaatcagtt taagctgatt   2040
ctgaacggtg cgtacggcaa attcggcacc aaacaaaaca agaagagaaa agatttgatc   2100
atggataaga acggtttgct gaccttcacg ggtagcgtca cggaatacga gggtaaagaa   2160
ttctatcgtc cgtatgcgag cttcgttact gcctatggtc gcctgcaact gtggaacgcg   2220
attatctacg cggttggtgt ggagaatttt ctgtactgcg acaccgacag catctattgt   2280
aaccgtgaag ttaacagcct cattgaggat atgaacgcca ttggtgaaac catcgataaa   2340
acgattctgg gtaaatggga cgtggagcat gtctttgata agtttaaggt cctgggccag   2400
aagaagtaca tgtatcatga ttgcaaagaa gataaaacgg acctgaagtg ttgcggtctg   2460
ccgagcgatg cccgtaagat tatcattggt caaggtttcg acgagtttta tctgggcaaa   2520
aatgtcgaag gtaagaagca acgcaaaaaa gtgatcggcg ttgcctgctg ctggacacc    2580 ctgtttacga tcaagaaaat catgttctaa                                    2610
```

<210> SEQ ID NO 6
<211> LENGTH: 869
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Met His His His His His His His Ser Gly Asp Tyr Asp Ile Pro
1               5                   10                  15

Thr Thr Glu Asn Leu Tyr Phe Gln Gly Ala Met Val Asp Thr Leu Ser
            20                  25                  30

Gly Leu Ser Ser Glu Gln Gly Gln Ser Gly Asp Met Thr Ile Glu Glu
        35                  40                  45

Asp Ser Ala Thr His Ile Lys Phe Ser Lys Arg Asp Glu Asp Gly Lys
    50                  55                  60

Glu Leu Ala Gly Ala Thr Met Glu Leu Arg Asp Ser Ser Gly Lys Thr
65                  70                  75                  80

Ile Ser Thr Trp Ile Ser Asp Gly Gln Val Lys Asp Phe Tyr Leu Tyr
                85                  90                  95

Pro Gly Lys Tyr Thr Phe Val Glu Thr Ala Ala Pro Asp Gly Tyr Glu
            100                 105                 110

Val Ala Thr Ala Ile Thr Phe Thr Val Asn Glu Gln Gly Gln Val Thr
        115                 120                 125

Val Asn Gly Lys Ala Thr Lys Gly Asp Ala His Ile Gly Gly Ser Asp
    130                 135                 140

Lys His Thr Gln Tyr Val Lys Glu His Ser Phe Asn Tyr Asp Glu Tyr
145                 150                 155                 160

Lys Lys Ala Asn Phe Asp Lys Ile Glu Cys Leu Ile Phe Ala Thr Glu
                165                 170                 175

Ser Cys Thr Asn Tyr Glu Asn Asp Asn Thr Gly Ala Arg Val Tyr Gly
            180                 185                 190

Trp Gly Leu Gly Val Thr Arg Asn His Asn Met Ile Tyr Gly Gln Asn
        195                 200                 205
```

```
Leu Asn Gln Phe Trp Glu Val Cys Gln Asn Ile Phe Asn Asp Trp Tyr
210                 215                 220

His Asp Asn Lys His Thr Ile Lys Ile Thr Lys Thr Lys Lys Gly Phe
225                 230                 235                 240

Pro Lys Arg Lys Tyr Ile Lys Phe Pro Ile Ala Val His Asn Leu Gly
                245                 250                 255

Trp Asp Val Glu Phe Leu Lys Tyr Ser Leu Val Glu Asn Gly Phe Asn
                260                 265                 270

Tyr Asp Lys Gly Leu Leu Lys Thr Val Phe Ser Lys Gly Ala Pro Tyr
                275                 280                 285

Gln Thr Val Thr Asp Val Glu Glu Pro Lys Thr Phe His Ile Val Gln
290                 295                 300

Asn Asn Asn Ile Val Tyr Gly Cys Asn Val Tyr Met Asp Lys Phe Phe
305                 310                 315                 320

Glu Val Glu Asn Lys Asp Gly Ser Thr Thr Glu Ile Gly Leu Cys Leu
                325                 330                 335

Asp Phe Phe Asp Ser Tyr Lys Ile Ile Thr Cys Ala Glu Ser Gln Phe
                340                 345                 350

His Asn Tyr Val His Asp Val Asp Pro Met Phe Tyr Lys Met Gly Glu
                355                 360                 365

Glu Tyr Asp Tyr Asp Thr Trp Arg Ser Pro Thr His Lys Gln Thr Thr
                370                 375                 380

Leu Glu Leu Arg Tyr Gln Tyr Asn Asp Ile Tyr Met Leu Arg Glu Val
385                 390                 395                 400

Ile Glu Gln Phe Tyr Ile Asp Gly Leu Cys Gly Gly Glu Leu Pro Leu
                405                 410                 415

Thr Gly Met Arg Thr Ala Ser Ser Ile Ala Phe Asn Val Leu Lys Lys
                420                 425                 430

Met Thr Phe Gly Glu Glu Lys Thr Glu Glu Gly Tyr Ile Asn Tyr Phe
                435                 440                 445

Glu Leu Asp Lys Lys Thr Lys Phe Glu Phe Leu Arg Lys Arg Ile Glu
450                 455                 460

Met Glu Ser Tyr Thr Gly Gly Tyr Thr His Ala Asn His Lys Ala Val
465                 470                 475                 480

Gly Lys Thr Ile Asn Lys Ile Gly Cys Ser Leu Asp Ile Asn Ser Ala
                485                 490                 495

Tyr Pro Ser Gln Met Ala Tyr Lys Val Phe Pro Tyr Gly Lys Pro Val
                500                 505                 510

Arg Lys Thr Trp Gly Arg Lys Pro Lys Thr Glu Lys Asn Glu Val Tyr
                515                 520                 525

Leu Ile Glu Val Gly Phe Asp Phe Val Glu Pro Lys His Glu Glu Tyr
                530                 535                 540

Ala Leu Asp Ile Phe Lys Ile Gly Ala Val Asn Ser Lys Ala Leu Ser
545                 550                 555                 560

Pro Ile Thr Gly Ala Val Ser Gly Gln Glu Tyr Phe Cys Thr Asn Ile
                565                 570                 575

Lys Asp Gly Lys Ala Ile Pro Val Tyr Lys Glu Leu Lys Asp Thr Lys
                580                 585                 590

Leu Thr Thr Asn Tyr Asn Val Val Leu Thr Ser Val Glu Tyr Glu Phe
                595                 600                 605

Trp Ile Lys His Phe Asn Phe Gly Val Phe Lys Lys Asp Glu Tyr Asp
610                 615                 620
```

```
Cys Phe Glu Val Asp Asn Leu Glu Phe Thr Gly Leu Lys Ile Gly Ser
625                 630                 635                 640

Ile Leu Tyr Tyr Lys Ala Glu Lys Gly Lys Phe Lys Pro Tyr Val Asp
            645                 650                 655

His Phe Met Lys Met Lys Val Glu Asn Lys Lys Leu Gly Asn Lys Pro
            660                 665                 670

Leu Thr Asn Gln Phe Lys Leu Ile Leu Asn Gly Ala Tyr Gly Lys Phe
            675                 680                 685

Gly Thr Lys Gln Asn Lys Glu Lys Asp Leu Ile Met Asp Lys Asn
690                 695                 700

Gly Leu Leu Thr Phe Thr Gly Ser Val Thr Lys Tyr Glu Gly Lys Glu
705                 710                 715                 720

Phe Tyr Arg Pro Tyr Ala Ser Phe Val Thr Ala Tyr Gly Arg Leu Gln
            725                 730                 735

Leu Trp Asn Ala Ile Ile Tyr Ala Val Gly Val Glu Asn Phe Leu Tyr
            740                 745                 750

Cys Asp Thr Asp Ser Ile Tyr Cys Asn Arg Glu Val Asn Ser Leu Ile
            755                 760                 765

Glu Asp Met Asn Ala Ile Gly Glu Thr Ile Asp Lys Thr Ile Leu Gly
770                 775                 780

Lys Trp Asp Val Glu His Val Phe Asp Lys Phe Lys Val Leu Gly Gln
785                 790                 795                 800

Lys Lys Tyr Met Tyr His Asp Cys Lys Glu Asp Lys Thr Asp Leu Lys
            805                 810                 815

Cys Cys Gly Leu Pro Ser Asp Ala Arg Lys Ile Ile Gly Gln Gly
            820                 825                 830

Phe Asp Glu Phe Tyr Leu Gly Lys Asn Val Glu Gly Lys Lys Gln Arg
            835                 840                 845

Lys Lys Val Ile Gly Gly Cys Leu Leu Leu Asp Thr Leu Phe Thr Ile
850                 855                 860

Lys Lys Ile Met Phe
865

<210> SEQ ID NO 7
<211> LENGTH: 869
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met His His His His His His Ser Gly Asp Tyr Asp Ile Pro
1               5                   10                  15

Thr Thr Glu Asn Leu Tyr Phe Gln Gly Ala Met Val Asp Thr Leu Ser
                20                  25                  30

Gly Leu Ser Ser Glu Gln Gly Gln Ser Gly Asp Met Thr Ile Glu Glu
            35                  40                  45

Asp Ser Ala Thr His Ile Lys Phe Ser Lys Arg Asp Glu Asp Gly Lys
50                  55                  60

Glu Leu Ala Gly Ala Thr Met Glu Leu Arg Asp Ser Ser Gly Lys Thr
65                  70                  75                  80

Ile Ser Thr Trp Ile Ser Asp Gly Gln Val Lys Asp Phe Tyr Leu Tyr
                85                  90                  95

Pro Gly Lys Tyr Thr Phe Val Glu Thr Ala Ala Pro Asp Gly Tyr Glu
            100                 105                 110
```

```
Val Ala Thr Ala Ile Thr Phe Thr Val Asn Glu Gln Gly Gln Val Thr
        115                 120                 125

Val Asn Gly Lys Ala Thr Lys Gly Asp Ala His Ile Gly Gly Ser Asp
    130                 135                 140

Lys His Thr Gln Tyr Val Lys Glu His Ser Phe Asn Tyr Asp Glu Tyr
145                 150                 155                 160

Lys Lys Ala Asn Phe Asp Lys Ile Glu Cys Leu Ile Phe Ala Thr Glu
                165                 170                 175

Ser Cys Thr Asn Tyr Glu Asn Asp Asn Thr Gly Ala Arg Val Tyr Gly
            180                 185                 190

Trp Gly Leu Gly Val Thr Arg Asn His Asn Met Ile Tyr Gly Gln Asn
        195                 200                 205

Leu Asn Gln Phe Trp Glu Val Cys Gln Asn Ile Phe Asn Asp Trp Tyr
    210                 215                 220

His Asp Asn Lys His Thr Ile Lys Ile Thr Lys Thr Lys Lys Gly Phe
225                 230                 235                 240

Pro Lys Arg Lys Tyr Ile Lys Phe Pro Ile Ala Val His Asn Leu Gly
                245                 250                 255

Trp Asp Val Glu Phe Leu Lys Tyr Ser Leu Val Glu Asn Gly Phe Asn
            260                 265                 270

Tyr Asp Lys Gly Leu Leu Lys Thr Val Phe Ser Lys Gly Ala Pro Tyr
        275                 280                 285

Gln Thr Val Thr Asp Val Glu Glu Pro Lys Thr Phe His Ile Val Gln
    290                 295                 300

Asn Asn Asn Ile Val Tyr Gly Cys Asn Val Tyr Met Asp Lys Phe Phe
305                 310                 315                 320

Glu Val Glu Asn Lys Asp Gly Ser Thr Thr Glu Ile Gly Leu Cys Leu
                325                 330                 335

Asp Phe Phe Asp Ser Tyr Lys Ile Ile Thr Cys Ala Glu Ser Gln Phe
            340                 345                 350

His Asn Tyr Val His Asp Val Asp Pro Met Phe Tyr Lys Met Gly Glu
        355                 360                 365

Glu Tyr Asp Tyr Asp Thr Trp Arg Ser Pro Thr His Lys Gln Thr Thr
    370                 375                 380

Leu Glu Leu Arg Tyr Gln Tyr Asn Asp Ile Tyr Met Leu Arg Glu Val
385                 390                 395                 400

Ile Glu Gln Phe Tyr Ile Asp Gly Leu Cys Gly Gly Glu Leu Pro Leu
                405                 410                 415

Thr Gly Met Arg Thr Ala Ser Ser Ile Ala Phe Asn Val Leu Lys Lys
            420                 425                 430

Met Thr Phe Gly Glu Glu Lys Thr Glu Glu Gly Tyr Ile Asn Tyr Phe
        435                 440                 445

Glu Leu Asp Lys Lys Thr Lys Phe Glu Phe Leu Arg Lys Arg Ile Glu
    450                 455                 460

Met Glu Ser Tyr Thr Gly Gly Tyr Thr His Ala Asn His Lys Ala Val
465                 470                 475                 480

Gly Lys Thr Ile Asn Lys Ile Gly Cys Ser Leu Asp Ile Asn Ser Ala
                485                 490                 495

Tyr Pro Ser Gln Met Ala Tyr Lys Val Phe Pro Tyr Gly Lys Pro Val
            500                 505                 510
```

Arg Lys Thr Trp Gly Arg Lys Pro Lys Thr Glu Lys Asn Glu Val Tyr
515                 520                 525

Leu Ile Glu Val Gly Phe Asp Phe Val Glu Pro Lys His Glu Glu Tyr
530                 535                 540

Ala Leu Asp Ile Phe Lys Ile Gly Ala Val Asn Ser Lys Ala Leu Ser
545                 550                 555                 560

Pro Ile Thr Gly Ala Val Ser Gly Gln Glu Tyr Phe Cys Thr Asn Ile
                565                 570                 575

Lys Asp Gly Lys Ala Ile Pro Val Tyr Lys Glu Leu Lys Asp Thr Lys
                580                 585                 590

Leu Thr Thr Asn Tyr Asn Val Val Leu Thr Ser Val Glu Tyr Glu Phe
                595                 600                 605

Trp Ile Lys His Phe Asn Phe Gly Val Phe Lys Lys Asp Glu Tyr Asp
610                 615                 620

Cys Phe Glu Val Asp Asn Leu Glu Phe Thr Gly Leu Lys Ile Gly Ser
625                 630                 635                 640

Ile Leu Tyr Tyr Lys Ala Glu Lys Gly Lys Phe Lys Pro Tyr Val Asp
                645                 650                 655

His Phe Met Lys Met Lys Val Glu Asn Lys Lys Leu Gly Asn Lys Pro
                660                 665                 670

Leu Thr Asn Gln Phe Lys Leu Ile Leu Asn Gly Ala Tyr Gly Lys Phe
                675                 680                 685

Gly Thr Lys Gln Asn Lys Glu Glu Lys Asp Leu Ile Met Asp Lys Asn
690                 695                 700

Gly Leu Leu Thr Phe Thr Gly Ser Val Thr Lys Tyr Glu Gly Lys Glu
705                 710                 715                 720

Phe Tyr Arg Pro Tyr Ala Ser Phe Val Thr Ala Tyr Gly Arg Leu Gln
                725                 730                 735

Leu Trp Asn Ala Ile Ile Tyr Ala Val Gly Val Glu Asn Phe Leu Tyr
                740                 745                 750

Cys Asp Thr Asp Ser Ile Tyr Cys Asn Arg Glu Val Asn Ser Leu Ile
                755                 760                 765

Glu Asp Met Asn Ala Ile Gly Glu Thr Ile Asp Lys Thr Ile Leu Gly
770                 775                 780

Lys Trp Asp Val Glu His Val Phe Asp Lys Phe Lys Val Leu Gly Gln
785                 790                 795                 800

Lys Lys Tyr Met Tyr His Asp Cys Lys Glu Asp Lys Thr Asp Leu Lys
                805                 810                 815

Cys Cys Gly Leu Pro Ser Asp Ala Arg Lys Ile Ile Ile Gly Gln Gly
                820                 825                 830

Phe Asp Glu Phe Tyr Leu Gly Lys Asn Val Glu Gly Lys Lys Gln Arg
                835                 840                 845

Lys Lys Val Ile Gly Gly Cys Leu Leu Leu Asp Thr Lys Phe Thr Ile
850                 855                 860

Lys Lys Ile Met Phe
865

<210> SEQ ID NO 8
<211> LENGTH: 869
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met His His His His His His Ser Gly Asp Tyr Asp Ile Pro
1               5                   10                  15

Thr Thr Glu Asn Leu Tyr Phe Gln Gly Ala Met Val Asp Thr Leu Ser
            20                  25                  30

Gly Leu Ser Ser Glu Gln Gly Gln Ser Gly Asp Met Thr Ile Glu Glu
        35                  40                  45

Asp Ser Ala Thr His Ile Lys Phe Ser Lys Arg Asp Glu Asp Gly Lys
    50                  55                  60

Glu Leu Ala Gly Ala Thr Met Glu Leu Arg Asp Ser Ser Gly Lys Thr
65                  70                  75                  80

Ile Ser Thr Trp Ile Ser Asp Gly Gln Val Lys Asp Phe Tyr Leu Tyr
                85                  90                  95

Pro Gly Lys Tyr Thr Phe Val Glu Thr Ala Ala Pro Asp Gly Tyr Glu
            100                 105                 110

Val Ala Thr Ala Ile Thr Phe Thr Val Asn Glu Gln Gly Gln Val Thr
        115                 120                 125

Val Asn Gly Lys Ala Thr Lys Gly Asp Ala His Ile Gly Gly Ser Asp
    130                 135                 140

Lys His Thr Gln Tyr Val Lys Glu His Ser Phe Asn Tyr Asp Glu Tyr
145                 150                 155                 160

Lys Lys Ala Asn Phe Asp Lys Ile Glu Cys Leu Ile Phe Ala Thr Glu
                165                 170                 175

Ser Cys Thr Asn Tyr Glu Asn Asp Asn Thr Gly Ala Arg Val Tyr Gly
            180                 185                 190

Trp Gly Leu Gly Val Thr Arg Asn His Asn Met Ile Tyr Gly Gln Asn
        195                 200                 205

Leu Asn Gln Phe Trp Glu Val Cys Gln Asn Ile Phe Asn Asp Trp Tyr
    210                 215                 220

His Asp Asn Lys His Thr Ile Lys Ile Thr Lys Thr Lys Gly Phe
225                 230                 235                 240

Pro Lys Arg Lys Tyr Ile Lys Phe Pro Ile Ala Val His Asn Leu Gly
            245                 250                 255

Trp Asp Val Glu Phe Leu Lys Tyr Ser Leu Val Glu Asn Gly Phe Asn
        260                 265                 270

Tyr Asp Lys Gly Leu Leu Lys Thr Val Phe Ser Lys Gly Ala Pro Tyr
    275                 280                 285

Gln Thr Val Thr Asp Val Glu Glu Pro Lys Thr Phe His Ile Val Gln
290                 295                 300

Asn Asn Asn Ile Val Tyr Gly Cys Asn Val Tyr Met Asp Lys Phe Phe
305                 310                 315                 320

Glu Val Glu Asn Lys Asp Gly Ser Thr Thr Glu Ile Gly Leu Cys Leu
            325                 330                 335

Asp Phe Phe Asp Ser Tyr Lys Ile Ile Thr Cys Ala Glu Ser Gln Phe
        340                 345                 350

His Asn Tyr Val His Asp Val Asp Pro Met Phe Tyr Lys Met Gly Glu
    355                 360                 365

Glu Tyr Asp Tyr Asp Thr Trp Arg Ser Pro Thr His Lys Gln Thr Thr
370                 375                 380

Leu Glu Leu Arg Tyr Gln Tyr Asn Asp Ile Tyr Met Leu Arg Glu Val
385                 390                 395                 400

Ile Glu Gln Phe Tyr Ile Asp Gly Leu Cys Gly Gly Glu Leu Pro Leu
                405                 410                 415
```

```
Thr Gly Met Arg Thr Ala Ser Ser Ile Ala Phe Asn Val Leu Lys Lys
            420                 425                 430

Met Thr Phe Gly Glu Glu Lys Thr Glu Glu Gly Tyr Ile Asn Tyr Phe
            435                 440                 445

Glu Leu Asp Lys Lys Thr Lys Phe Glu Phe Leu Arg Lys Arg Ile Glu
            450                 455                 460

Met Glu Ser Tyr Thr Gly Gly Tyr Thr His Ala Asn His Lys Ala Val
465                 470                 475                 480

Gly Lys Thr Ile Asn Lys Ile Gly Cys Ser Leu Asp Ile Asn Ser Ala
            485                 490                 495

Tyr Pro Ser Gln Met Ala Tyr Lys Val Phe Pro Tyr Gly Lys Pro Val
            500                 505                 510

Arg Lys Thr Trp Gly Arg Lys Pro Lys Thr Glu Lys Asn Glu Val Tyr
            515                 520                 525

Leu Ile Glu Val Gly Phe Asp Phe Val Glu Pro Lys His Glu Glu Tyr
            530                 535                 540

Ala Leu Asp Ile Phe Lys Ile Gly Ala Val Asn Ser Lys Ala Leu Ser
545                 550                 555                 560

Pro Ile Thr Gly Ala Val Ser Gly Gln Glu Tyr Phe Cys Thr Asn Ile
            565                 570                 575

Lys Asp Gly Lys Ala Ile Pro Val Tyr Lys Glu Leu Lys Asp Thr Lys
            580                 585                 590

Leu Thr Thr Asn Tyr Asn Val Val Leu Thr Ser Val Glu Tyr Glu Phe
            595                 600                 605

Trp Ile Lys His Phe Asn Phe Gly Val Phe Lys Lys Asp Glu Tyr Asp
            610                 615                 620

Cys Phe Glu Val Asp Asn Leu Glu Phe Thr Gly Leu Lys Ile Gly Ser
625                 630                 635                 640

Ile Leu Tyr Tyr Lys Ala Glu Lys Gly Lys Phe Lys Pro Tyr Val Asp
            645                 650                 655

His Phe Met Lys Met Lys Val Glu Asn Lys Lys Leu Gly Asn Lys Pro
            660                 665                 670

Leu Thr Asn Gln Phe Lys Leu Ile Leu Asn Gly Ala Tyr Gly Lys Phe
            675                 680                 685

Gly Thr Lys Gln Asn Lys Glu Glu Lys Asp Leu Ile Met Asp Lys Asn
690                 695                 700

Gly Leu Leu Thr Phe Thr Gly Ser Val Thr Lys Tyr Glu Gly Lys Glu
705                 710                 715                 720

Phe Tyr Arg Pro Tyr Ala Ser Phe Val Thr Ala Tyr Gly Arg Leu Gln
            725                 730                 735

Leu Trp Asn Ala Ile Ile Tyr Ala Val Gly Val Glu Asn Phe Leu Tyr
            740                 745                 750

Cys Asp Thr Asp Ser Ile Tyr Cys Asn Arg Glu Val Asn Ser Leu Ile
            755                 760                 765

Glu Asp Met Asn Ala Ile Gly Glu Thr Ile Asp Lys Thr Ile Leu Gly
            770                 775                 780

Lys Trp Asp Val Glu His Val Phe Asp Lys Phe Lys Val Leu Gly Gln
785                 790                 795                 800

Lys Lys Tyr Met Tyr His Asp Cys Lys Glu Asp Lys Thr Asp Leu Lys
            805                 810                 815

Cys Cys Gly Leu Pro Ser Asp Ala Arg Lys Ile Ile Ile Gly Gln Gly
            820                 825                 830
```

```
Phe Asp Glu Phe Tyr Leu Gly Lys Asn Val Glu Gly Lys Gln Arg
            835                 840                 845

Lys Lys Val Ile Gly Gly Cys Leu Leu Leu Asp Thr Leu Phe Thr Ile
    850                 855                 860

Lys Lys Ile Lys Phe
865

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5

<210> SEQ ID NO 10
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Gly Asp Tyr Asp Ile Pro Thr Thr Glu Asn Leu Tyr Phe Gln Gly
1               5                   10                  15

Ala Met Val Asp Thr Leu Ser Gly Leu Ser Ser Glu Gln Gly Gln Ser
            20                  25                  30

Gly Asp Met Thr Ile Glu Glu Asp Ser Ala Thr His Ile Lys Phe Ser
        35                  40                  45

Lys Arg Asp Glu Asp Gly Lys Glu Leu Ala Gly Ala Thr Met Glu Leu
    50                  55                  60

Arg Asp Ser Ser Gly Lys Thr Ile Ser Thr Trp Ile Ser Asp Gly Gln
65                  70                  75                  80

Val Lys Asp Phe Tyr Leu Tyr Pro Gly Lys Tyr Thr Phe Val Glu Thr
                85                  90                  95

Ala Ala Pro Asp Gly Tyr Glu Val Ala Thr Ala Ile Thr Phe Thr Val
            100                 105                 110

Asn Glu Gln Gly Gln Val Thr Val Asn Gly Lys Ala Thr Lys Gly Asp
        115                 120                 125

Ala His Ile
    130

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala His Ile Val Met Val Asp Ala Tyr Lys Pro Thr Lys
1               5                   10
```

```
<210> SEQ ID NO 12
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
agagtgatag tatgattatg tagatgtagg atttgatatg tgagtagccg aatgaaacct       60
t                                                                      61

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttttcataat catactatca ctct                                             24

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 1-3 'Gly Gly Gly
      Gly Ser' repeating units

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ser Lys Leu Gly
1               5

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ttggtttcat tcgg                                                        14
```